US012761202B2

United States Patent
(12) United States Patent
Garner et al.

(10) Patent No.: US 12,761,202 B2
(45) Date of Patent: Oct. 13, 2026

(54) MACHINE CONTROL BASED ON MEASURED SOIL STRENGTH

(71) Applicant: Deere & Company, Moline, IL (US)

(72) Inventors: Elijah B. Garner, Bettendorf, IA (US); Kelby J. Krueger, Geneseo, IL (US); Cary S. Hubner, Geneseo, IL (US); Michael C. Steele, Orion, IL (US); Bradley A. Wackerle, Delmar, IA (US)

(73) Assignee: Deere & Company, Moline, IL (US)

( * ) Notice: Subject to any disclaimer, the term of this patent is extended or adjusted under 35 U.S.C. 154(b) by 189 days.

(21) Appl. No.: 18/056,939

(22) Filed: Nov. 18, 2022

(65) Prior Publication Data

US 2024/0167998 A1 May 23, 2024

(51) Int. Cl.

| | |
|---|---|
| ***G01N 33/24*** | (2006.01) |
| ***A01B 49/06*** | (2006.01) |
| ***A01B 76/00*** | (2006.01) |
| ***A01C 21/00*** | (2006.01) |

(52) U.S. Cl.

CPC ............. *G01N 33/24* (2013.01); *A01B 49/06* (2013.01); *A01B 76/00* (2013.01); *A01C 21/00* (2013.01); *G01N 33/245* (2024.05)

(58) Field of Classification Search

CPC ...... G01N 33/24; G01N 33/245; A01C 7/006; A01C 7/205; A01C 21/00; A01C 5/064; A01C 5/068; A01B 49/06; A01B 76/00; A01B 79/005; A01B 63/008; A01B 63/111

See application file for complete search history.

(56) References Cited

U.S. PATENT DOCUMENTS

| | | | | |
|---|---|---|---|---|
| 6,325,156 | B1 | 12/2001 | Barry | |
| 6,647,799 | B1 | 11/2003 | Raper et al. | |
| 6,937,939 | B1 * | 8/2005 | Shibusawa ........... | G01N 33/246 356/336 |
| 8,078,367 | B2 * | 12/2011 | Sauder ................... | A01C 7/105 715/965 |
| 8,910,582 | B2 * | 12/2014 | Mariman ............... | A01C 7/205 111/190 |
| 8,985,232 | B2 | 3/2015 | Bassett | |
| 9,198,343 | B2 * | 12/2015 | Mariman ............... | A01C 21/00 |
| 9,826,677 | B2 * | 11/2017 | Gervais .................. | A01C 7/205 |
| 10,091,926 | B2 * | 10/2018 | Maro ..................... | A01C 7/205 |

(Continued)

FOREIGN PATENT DOCUMENTS

| | | | | |
|---|---|---|---|---|
| CN | 112729651 A | | 4/2021 | |
| EP | 0838139 A2 | * | 4/1998 | ........... A01B 63/023 |

(Continued)

OTHER PUBLICATIONS

Extended European Search Report and Written Opinion issued in European Patent Application No. 23210676.5 dated Apr. 15, 2024, in 10 pages.

(Continued)

*Primary Examiner* — Angelina M Shudy
*Assistant Examiner* — Mark Robert Heim
(74) *Attorney, Agent, or Firm* — Christopher J. Volkmann; KELLY, HOLT & CHRISTENSON PLLC

(57) ABSTRACT

An agricultural machine includes a soil strength generation system that generates an output indicator of soil strength. A control system generates on action signal based on the soil strength.

19 Claims, 13 Drawing Sheets

(56) References Cited

U.S. PATENT DOCUMENTS

| | | | | |
|---|---|---|---|---|
| 10,143,128 | B2 | 12/2018 | Landphair et al. | |
| 10,548,260 | B2 | 2/2020 | Bassett | |
| 10,561,059 | B2 * | 2/2020 | Levy | A01C 7/06 |
| 11,064,646 | B2 | 7/2021 | Zemenchik et al. | |
| 11,140,812 | B2 * | 10/2021 | Leimkuehler | A01B 63/111 |
| 11,224,153 | B2 * | 1/2022 | Leimkuehler | A01B 63/32 |
| 11,224,159 | B2 * | 1/2022 | Thompson | A01B 63/008 |
| 11,297,753 | B2 * | 4/2022 | Achen | A01C 7/205 |
| 12,457,921 | B2 * | 11/2025 | Krueger | A01B 76/00 |
| 12,543,615 | B2 * | 2/2026 | Garner | A01B 63/002 |
| 12,582,024 | B2 * | 3/2026 | Erker | A01C 7/203 |
| 2010/0198529 | A1 | 8/2010 | Sauder et al. | |
| 2012/0048160 | A1 * | 3/2012 | Adams | A01C 5/066 111/163 |
| 2012/0125244 | A1 * | 5/2012 | Beaujot | A01B 79/005 111/149 |
| 2012/0186503 | A1 * | 7/2012 | Sauder | A01C 7/205 701/50 |
| 2012/0232691 | A1 * | 9/2012 | Green | A01C 7/203 700/231 |
| 2013/0032363 | A1 * | 2/2013 | Curry | A01C 7/205 172/4 |
| 2013/0112121 | A1 * | 5/2013 | Achen | A01C 21/00 172/1 |
| 2013/0248212 | A1 | 9/2013 | Bassett | |
| 2014/0000919 | A1 * | 1/2014 | Bachman | A01B 63/114 172/4 |
| 2014/0048295 | A1 | 2/2014 | Bassett | |
| 2014/0048296 | A1 | 2/2014 | Bassett | |
| 2014/0116735 | A1 | 5/2014 | Bassett | |
| 2014/0214284 | A1 * | 7/2014 | Sauder | A01C 5/06 701/50 |
| 2015/0013579 | A1 * | 1/2015 | Mariman | A01C 7/203 111/59 |
| 2015/0105965 | A1 | 4/2015 | Blackwell et al. | |
| 2017/0034995 | A1 * | 2/2017 | Wilhelmi | A01C 7/20 |
| 2017/0086361 | A1 * | 3/2017 | Landphair | A01C 5/068 |
| 2017/0211597 | A1 * | 7/2017 | Vigholm | E02F 9/0883 |
| 2017/0265377 | A1 | 9/2017 | Landphair et al. | |
| 2017/0367251 | A1 * | 12/2017 | Hamilton | A01C 7/203 |
| 2018/0042171 | A1 * | 2/2018 | Maro | A01C 7/205 |
| 2018/0153091 | A1 * | 6/2018 | Hamilton | A01C 5/064 |
| 2018/0340845 | A1 | 11/2018 | Rhodes et al. | |
| 2019/0029165 | A1 * | 1/2019 | Leimkuehler | A01B 63/32 |
| 2019/0045703 | A1 * | 2/2019 | Bassett | A01C 5/066 |
| 2019/0183036 | A1 * | 6/2019 | Leimkuehler | A01C 5/062 |
| 2019/0327882 | A1 * | 10/2019 | Kowalchuk | A01C 7/205 |
| 2019/0373797 | A1 * | 12/2019 | Schoeny | A01C 5/068 |
| 2020/0000006 | A1 * | 1/2020 | Mcdonald | A01B 79/005 |
| 2020/0060068 | A1 * | 2/2020 | Stanhope | A01C 7/205 |
| 2020/0128723 | A1 | 4/2020 | Eichhorn | |
| 2020/0146208 | A1 * | 5/2020 | Bassett | A01B 79/005 |
| 2020/0154626 | A1 | 5/2020 | Schoeny et al. | |
| 2020/0154627 | A1 * | 5/2020 | Plattner | A01C 5/064 |
| 2020/0236843 | A1 | 7/2020 | Graham et al. | |
| 2020/0281111 | A1 * | 9/2020 | Walter | A01C 7/208 |
| 2020/0337205 | A1 * | 10/2020 | Maro | A01C 7/203 |
| 2020/0352080 | A1 | 11/2020 | Martin | |
| 2020/0396894 | A1 * | 12/2020 | Radtke | A01B 63/008 |
| 2021/0127549 | A1 | 5/2021 | Kinney et al. | |
| 2021/0131856 | A1 * | 5/2021 | Henry | A01B 15/16 |
| 2021/0153421 | A1 | 5/2021 | Holoubek et al. | |
| 2021/0179103 | A1 * | 6/2021 | Kowalchuk | B60W 50/14 |
| 2021/0219482 | A1 * | 7/2021 | Smith | A01B 76/00 |
| 2022/0000002 | A1 * | 1/2022 | Bassett | A01B 61/048 |
| 2022/0279697 | A1 * | 9/2022 | Johnson | A01C 7/205 |
| 2022/0295686 | A1 * | 9/2022 | Koch | A01B 79/005 |
| 2022/0330476 | A1 * | 10/2022 | Koch | A01B 47/00 |
| 2023/0041214 | A1 | 2/2023 | Bassett | |
| 2023/0337570 | A1 * | 10/2023 | Conboy | A01B 63/008 |
| 2024/0065132 | A1 | 2/2024 | Birkmann et al. | |
| 2024/0065137 | A1 * | 2/2024 | Erker | A01C 7/203 |
| 2024/0180066 | A1 | 6/2024 | Holoubek et al. | |

FOREIGN PATENT DOCUMENTS

| | | | |
|---|---|---|---|
| EP | 2497348 | A1 | 9/2012 |
| EP | 3398423 | A1 | 11/2018 |
| EP | 4256935 | A1 | 10/2023 |
| WO | 2016205421 | A1 | 12/2016 |
| WO | 2019092188 | A1 | 5/2019 |

OTHER PUBLICATIONS

Brune P.F., et al., "Relating Planter Downforce and Soil Strength," Soil and Tillage Research, Dec. 2018, vol. 184, pp. 243-252.

Cardei P., et al., "Validation and Ordering Test for an Formula of Soil Tillage Draft Force, Extended to the Dependence on Soil Moisture," IEEE Xplore, Nov. 2020, pp. 1-4.

Extended European Search Report for European Application No. 23210672.4, dated Apr. 5, 2024, in 12 Pages.

Extended European Search Report for European Application No. 23210679.9, dated Apr. 15, 2024, 10 Pages.

* cited by examiner

MACHINE CONTROL BASED ON MEASURED SOIL STRENGTH

FIELD OF THE DESCRIPTION

The present description generally relates to planting equipment. More specifically, but not by limitation, the present description relates to a control system configured to control an agricultural planting machine based on a measured soil strength.

BACKGROUND

There are a wide variety of different types of agricultural seeding or planting machines. Such machines can include row crop planters, grain drills, air seeders or the like. These machines place seeds at a desired depth within a plurality of parallel seed trenches or furrows that are formed in the soil. Thus, some of the machines can carry one or more seed hoppers and a plurality of row units. The row units are used for opening a furrow and moving the seed from the seed hopper to the ground. The row units can also close the furrow. The row units can include a seed metering system and a seed delivery system.

The seed metering system receives the seeds in a bulk manner and divides the seeds into smaller quantities (such as a single seed, or a small number of seeds—depending on the seed size and seed type) and delivers the metered seeds to the seed delivery system. There are different types of seed metering systems and, in one example, the seed metering system uses a rotating mechanism (which may be a disc or a concave or bowl-shaped mechanism) that has seed receiving apertures, that receive the seeds from a seed pool and move the seeds from the seed pool to the seed delivery system which delivers the seeds to the ground (or to a location below the surface of the ground, such as in a trench).

There are also different types of seed delivery systems that move the seed from the seed metering system to the ground. One seed delivery system is a gravity drop system that includes a seed tube that has an inlet positioned below the seed metering system. Metered seeds from the seed metering system are dropped into the seed tube and fall (via gravitational force) through the seed tube into the seed trench. Other types of seed delivery systems are assistive systems, in that they do not simply rely on gravity to move the seed from the metering mechanism into the ground. Instead, such systems actively capture the seeds from the seed meter and physically move the seeds from the meter to a lower opening, where the seeds exit into the ground or trench.

In these types of planting machines, the row units have a controllable downforce actuator that is actuated to exert downforce on the row unit. The row unit includes controllable gage wheels that are configured to control the depth of the furrow and thus the depth of the planted seed.

The discussion above is merely provided for general background information and is not intended to be used as an aid in determining the scope of the claimed subject matter.

SUMMARY

An agricultural machine includes a soil strength generation system that generates an output indicative of soil strength. A control system controls a downforce actuator to control downforce on a row unit based on the soil strength.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

Figure 1:
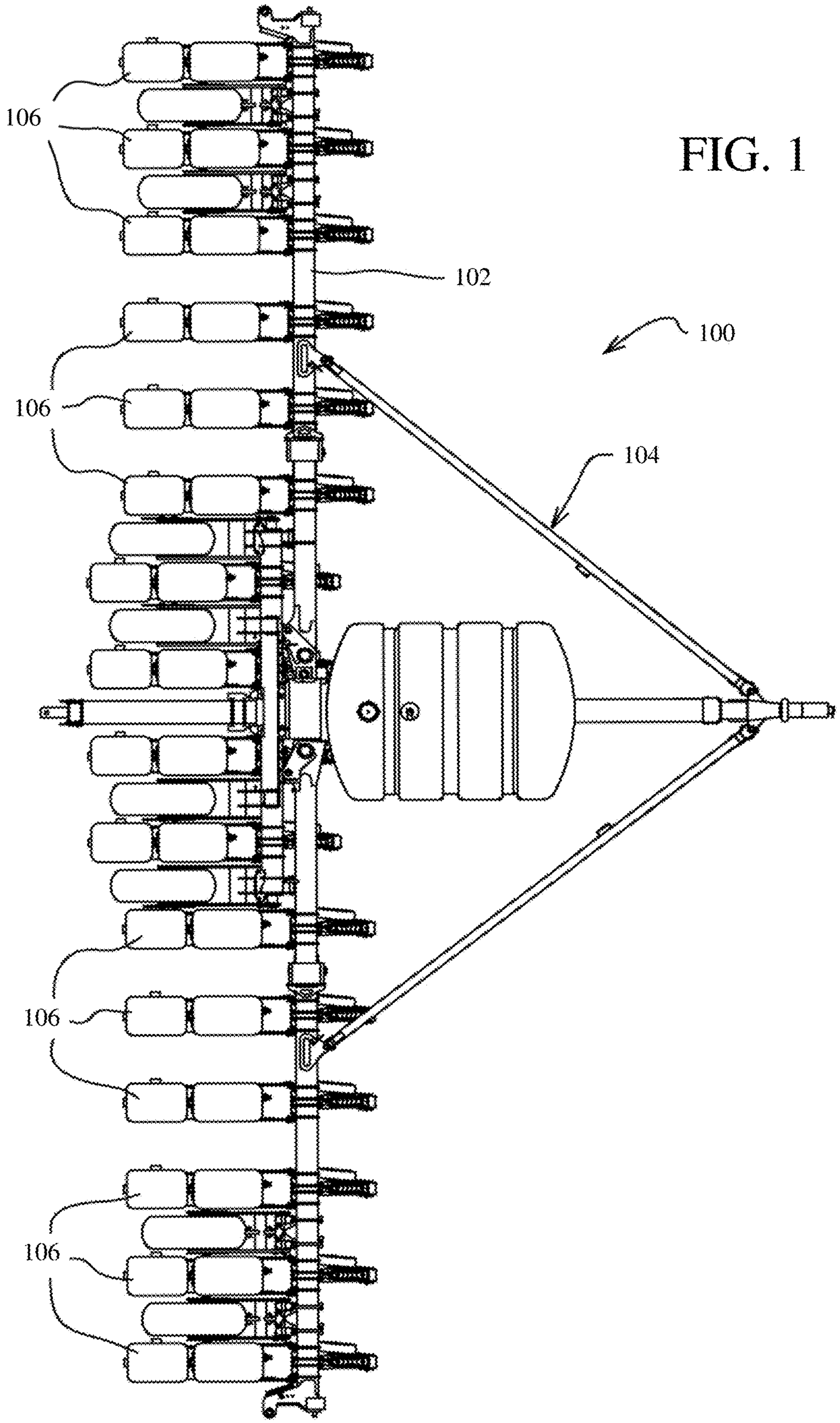
FIG. 1 shows one example of a top view of an agricultural machine.

The present description generally relates to planting equipment. An example agricultural planting machine includes a row unit with a seeding system that meters seeds from a source and delivers the metered seeds to a furrow or trench formed in the ground.

The row units also have a downforce actuator that is used to apply downforce to the row unit in order to assist in controlling the depth of the furrow or trench opened by the row unit. The row unit has gage wheels that are used to limit the depth of penetration of the furrow opener. The amount of downforce needed to obtain desired planting performance can be dependent on soil strength. Soil strength (which is also sometimes referred to as soil resistance or soil compaction) has often been measured by a cone penetrometer which involves measuring the force needed to drive a cone of a known geometry to a certain depth within the soil. The soil strength may be different under different circumstances. For instance, the soil strength may differ in tilled soil verses that in no-till environments. Similarly, the soil strength may differ based upon the level of soil compaction, the soil type, the soil moisture, other soil characteristics, and under a wide variety of other circumstances.

Currently, an operator of a planting machine often manually sets the downforce to a certain value upon entering a field, and that downforce value is often used throughout the entire field. Some current systems automatically adjust downforce, but those systems also automatically adjust the downforce to maintain a manually set downforce value. These types of downforce control systems can be less effective in achieving desired seeding performance for a number of reasons. For instance, the soil or field conditions may change during the planting operation, even in a single field. Also, the operator may be unfamiliar with the field or planting conditions thus making it difficult to set the downforce correctly. Also, the conditions throughout the field frequently change. For instance, the soil can vary between tilled and untitled soil, the soil type can change, the level of residue can change, the degree of soil compaction can vary, all within a single field. Thus, the soil strength may change drastically even within a single field. Also, the downforce may be set so that the planter assumes a "smile" configuration in which the center of the planter is forced closer to the soil while the outer edges of the planter rise, sometimes losing contact with the soil. Further, the effective soil strength may vary based upon the speed of the planting machine. For instance, even though the static soil strength (the soil strength measured without moving) may remain constant across a field, it may require additional downforce to achieve desired planting performance as the speed of the planting machine increases.

The present system thus includes a system that automatically measures or estimates an indicator of soil strength on-the-go, while the planting machine is traveling through the field performing the planting operation. The present discussion describes calculating "soil strength" but it will be understood that the term "soil strength" includes metrics that are proxies for soil strength or indicators of soil strength, such as soil resistance, soil compaction, the force needed for a ground engaging element to penetrate the ground to a desired depth or other proxies for, or indicators of, soil strength. Also, by automatically it is meant that the operation or function is performed without further human involvement except perhaps to authorize or initiate the operation or function. An action signal can be generated to control downforce/upforce based upon the measured or estimated soil strength.

Further, the action signal can be generated (or the soil strength indicator can be generated) based on a wide variety of other criteria, such as the speed of the planter, soil characteristics, the characteristics of the furrow (where those characteristics are sensed), based on the compaction level of the soil, the settings that were used during a prior pass at a similar location in the field, and based on other criteria. The particular action performed based on the action signal or control signal can also vary. The control signal may be generated to control downforce or up force applied to the planting machine by an actuator either on an individual row unit basis or to control the downforce or up force applied to a set of row units. The action signal can be used to control downforce or upforce applied to other ground engaging elements, such as a row cleaner, the furrow opener, a seed firmer, a furrow closer, a colter, fertilizer opener, etc. The action signal can be generated to control a tire inflation system, a frame weight distribution system, a fill control system that controls the level of seed, nutrients or other material filled into tanks that are carried by the planting machine, to control machine configuration (such as spring stiffness or the angle of engagement of ground engaging elements), the speed of the agricultural vehicle, the route or path taken by the agricultural vehicle, among other things. The action signal can be generated to communicate the soil strength setting (and optionally other settings, such as downforce settings, etc.) to a mapping system or route planning system that can be used to generate maps of soil strength, to generate routes for the current or subsequent agricultural operations, etc.

FIG. 1 is a top view of one example of an agricultural machine 100. Agricultural machine 100 is a towed implement that illustratively includes a toolbar 102 that is part of a frame 104. FIG. 1 also shows that a plurality of row units 106 are mounted to the toolbar. Agricultural machine 100 can be towed behind another machine, such as a tractor (the towing vehicle).

Figure 2:
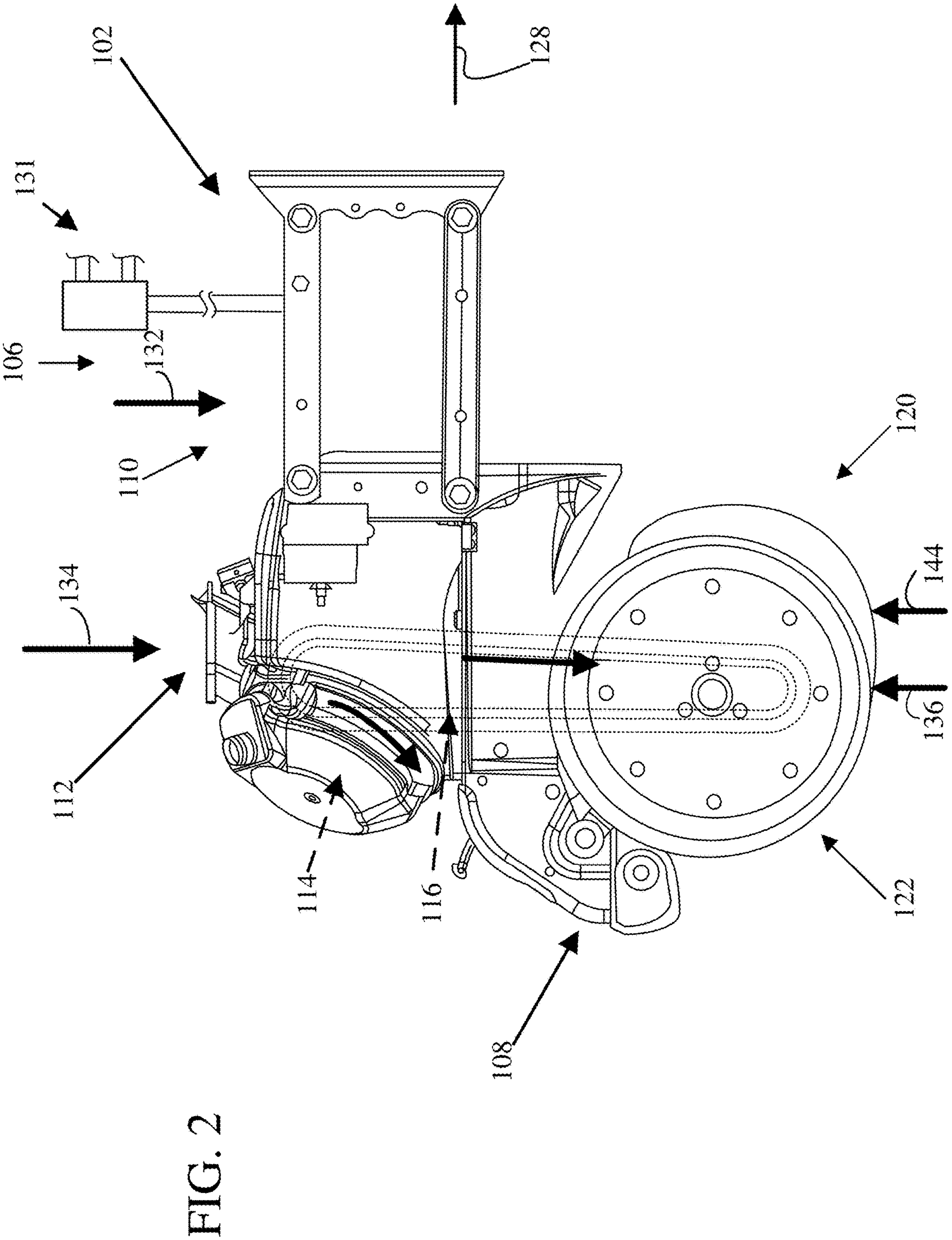
FIGS. 2-7 show example of a side view of a row unit of the agricultural machine shown in FIG. 1.

FIG. 2 is a side view showing one example of a row unit 106 (or a portion of row unit 106) in more detail. FIG. 2 shows that each row unit 106 illustratively has a frame 108. Frame 108 is illustratively connected to toolbar 102 by a linkage shown generally at 110. Linkage 110 is illustratively mounted to toolbar 102 so that it can move upwardly and downwardly (relative to toolbar 102).

Row unit 106 also illustratively has a seed hopper 112 that receives or stores seed. The seed is provided from hopper 112 to a seed metering system 114 that meters the seed and provides the metered seed to a seed delivery system 116 that delivers the seed from the seed metering system 114 to the furrow or trench generated by the row unit. In one example, seed metering system 114 uses a rotatable member, such as a disc or concave-shaped rotating member, and an air pressure differential to retain seed on the disc and move the seed from a seed pool of seeds (provided from hopper 112) to the seed delivery system 116. Other types of meters can be used as well. Row unit 106 can also include an additional hopper that can be used to provide additional material, such as a fertilizer or another chemical.

Row unit 106 includes furrow opener 120 and a set of gage wheels 122. In operation, row unit 106 moves generally in a direction indicated by arrow 128. Furrow opener 120 has blades or disks that open a furrow on the soil. Gage wheels 122 control a depth of the furrow, and seed is metered by seed metering system 114 and delivered to the furrow by seed delivery system 116. A downforce/upforce generator (or actuator) 131 can also be provided to controllably exert downforce/upforce to keep the row unit 106 in desired engagement with the soil. Downforce/upforce generator 131 can be a single acting actuator (e.g., to only apply downforce), or a plurality of single acting actuators (e.g., one for downforce and one for upforce), a double acting actuator, such as a double acting hydraulic cylinder, a pneumatic actuator, or another actuator that transfers downforce (and/or upforce) from toolbar 102 to row unit 106. Downforce/upforce generator 131 may also be referred to herein as downforce/upforce actuator 131, downforce actuator 131 or actuator 131.

Therefore, in one example, the downforce acting on row unit 106 includes the row unit downforce (or upforce) generated by downforce/upforce actuator 131 represented by arrow 132 in FIG. 2. The downforce acting on row unit 106 also includes the self-weight of row unit 106 and the components of row unit 106 as represented by arrow 134 in FIG. 2. The downforces 132 and 134 are countered by the force that the ground exerts on the blades on furrow opener 120 that are opening the furrow in the soil, as represented by arrow 144 in FIG. 2. The downforces 132 and 134 are also countered by the force that the ground exerts on the gage wheels 122 (the gage wheel reaction force) indicated by arrow 136 in FIG. 2. Therefore, in one example, an indication of soil strength can be obtained for the row unit 106 shown in FIG. 2 as the force needed to push the blades on furrow opener 120 into the ground by a depth set by gage wheels 122 and to reach a desired gage wheel reaction force 136, as indicated by Equation 1 below:

$$\text{SoilStrength} = \text{RUDF} + \text{SelfWeight} - \text{GWReactionForce} \quad \text{EQ. 1}$$

where RUDF is the row unit downforce (or upforce) represented by arrow 132;

SelfWeight is the weight of row unit 106 and its suspended components represented by arrows 134; and GWReactionForce is the gage wheel reaction force represented by arrow 136.

Figure 3:
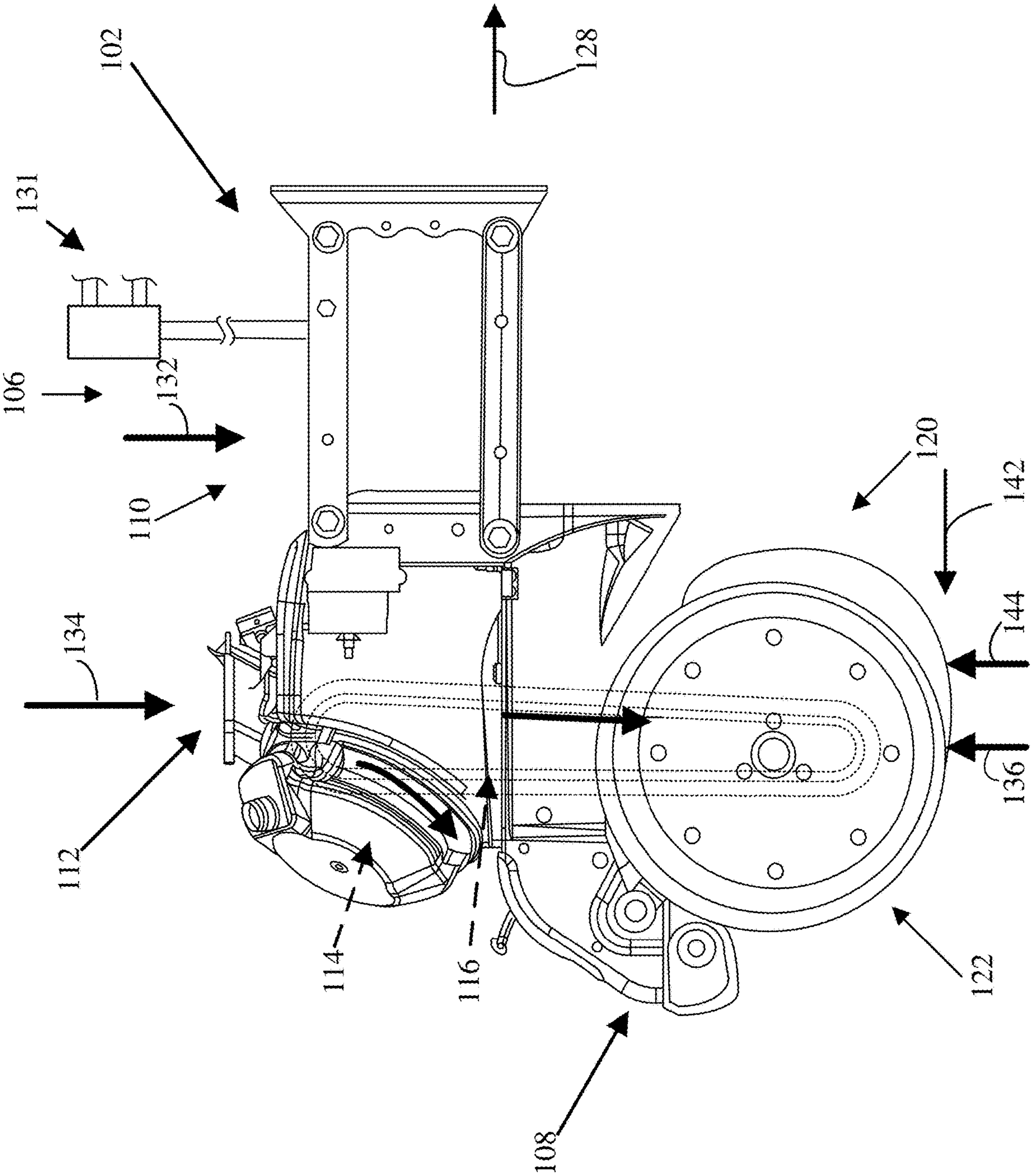

FIG. 3 is similar to FIG. 2 and similar items are similarly numbered. FIG. 3 shows that, in one example, a draft force (the force required to pull row unit 106 as it engages the ground) is exerted on the row unit 106 as indicated by arrow 142. In another example, where the parallel arms of linkage 110 are generally parallel to the ground, as shown in FIG. 3, the draft force 142 causes the round opener blades on furrow opener 120 to tend to roll up and over the ground, instead of continuing to penetrate the ground. In another example in which the parallel arms in linkage 110 extend away from tool bar 102 and are angled downwardly toward the ground, draft force 142 can cause row unit 106 to tend to rotate upward about its axes of rotation, defined by its connection points to tool 102, out of engagement with the ground. In these examples, the draft force can thus have an upward component that tends to lift the blades of furrow opener 120 up and out of the ground.

The draft force 142 increases in magnitude with the travel speed of row unit 106. Therefore, the upward component of the draft force which acts against the downforce on row unit 106 and the magnitude of the upward component also varies with the speed at which row unit 106 is traveling over the ground. The magnitude of the upward component of the draft force at different speeds can also vary with soil characteristics and other factors. The magnitude of the upward component of the draft force can be determined empirically or experimentally or in other ways and can be accounted for as follows:

$$\text{SoilStrength}=\text{RUDF}+\text{SelfWeight}-\text{GWReactionForce}-\text{DraftF} \quad \text{EQ. 2}$$

where DraftF is the upward component of the draft force.

Figure 4:
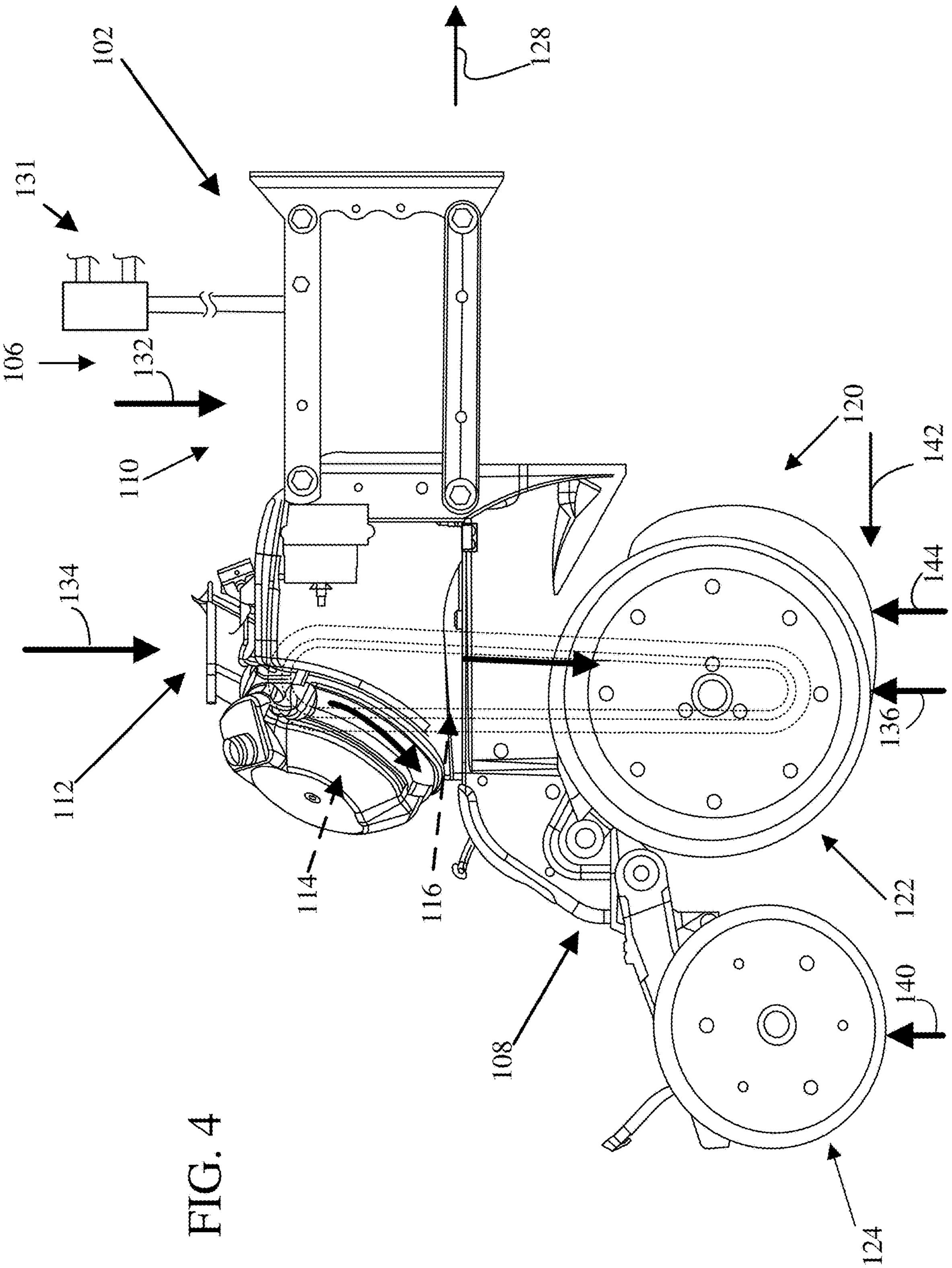

FIG. 4 is similar to FIG. 3 and similar items are similarly numbered. However, FIG. 4 also shows that row unit 106 includes closing wheels 124. Closing wheels 124 close the furrow that is opened by furrow opener 120, over the seed. In the example shown in FIG. 4, the downforce exerted on row unit 106 is also countered by the upwardly directed force imparted on closing wheels 124, as represented by arrow 140 in FIG. 4. Thus, an indicator of soil strength can be calculated as follows:

$$\text{SoilStrength}=\text{RUDF}+\text{SelfWeight}-\text{GWReactionForce}-\text{DraftF}-\text{CWF} \quad \text{EQ. 3}$$

where CWF is the upward force on closing wheels 124 as indicated by arrow 140 in FIG. 4.

Figure 5:
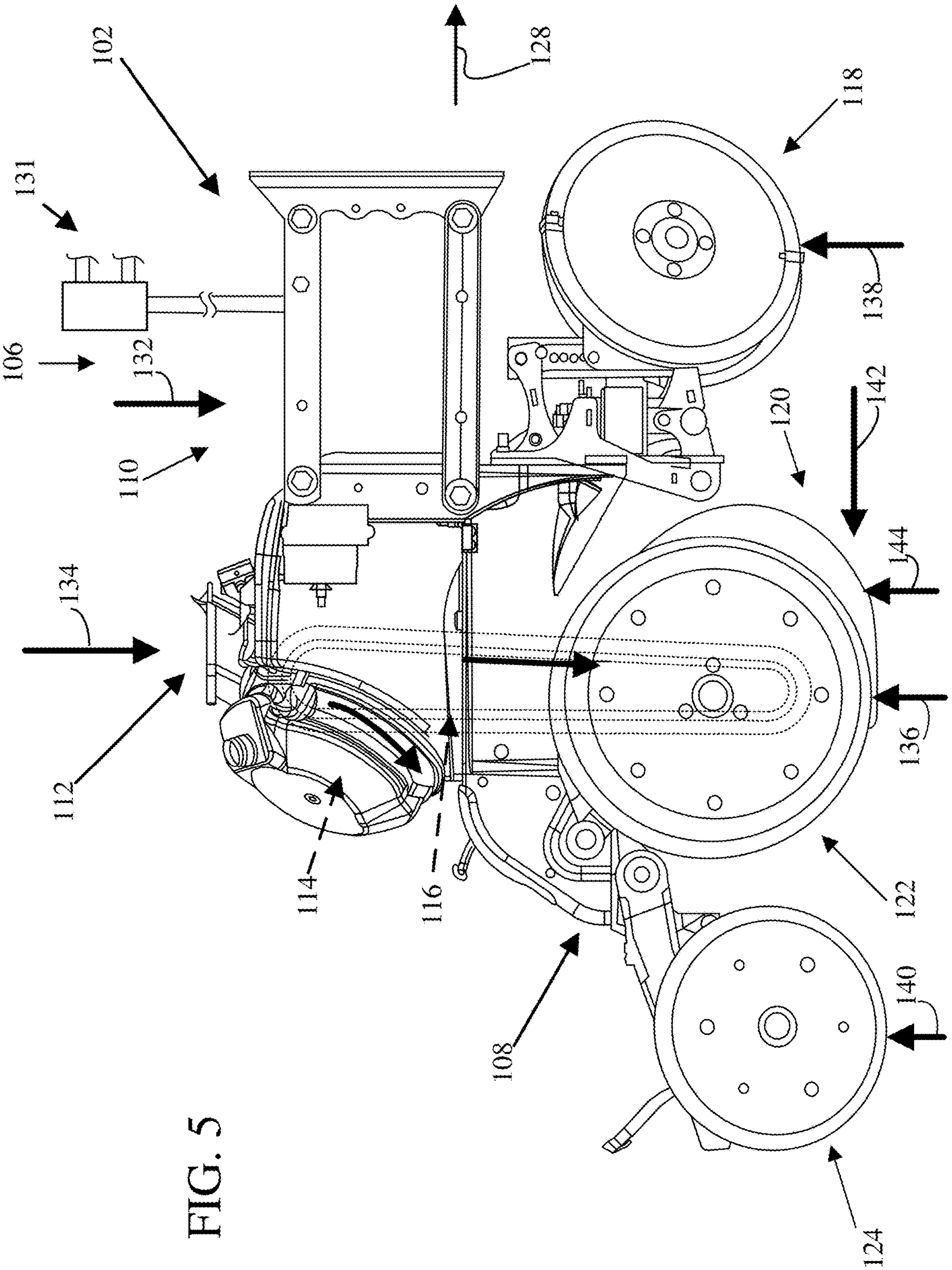

FIG. 5 is similar to FIG. 4, and similar items are similarly numbered. However, FIG. 5 shows that row unit 106 now includes a row cleaner 118. Row cleaner 118 generally cleans the row ahead of the opener 120 to remove plant debris and other items from the previous growing season. Therefore, the downforce on row unit 106 is also countered by an upwardly directed force that the ground exerts on row cleaner 118, as indicated by arrow 138. Thus, in the example shown in FIG. 5, an indicator of soil strength can be calculated as follows:

$$\text{SoilStrength}=\text{RUDF}+\text{SelfWeight}-\text{GWReactionForce}-\text{DraftF}-\text{CWF}-\text{CRF} \quad \text{EQ. 4}$$

where RCF is the upwardly directed force on row cleaner 118, as indicated by arrow 138.

Figure 6:
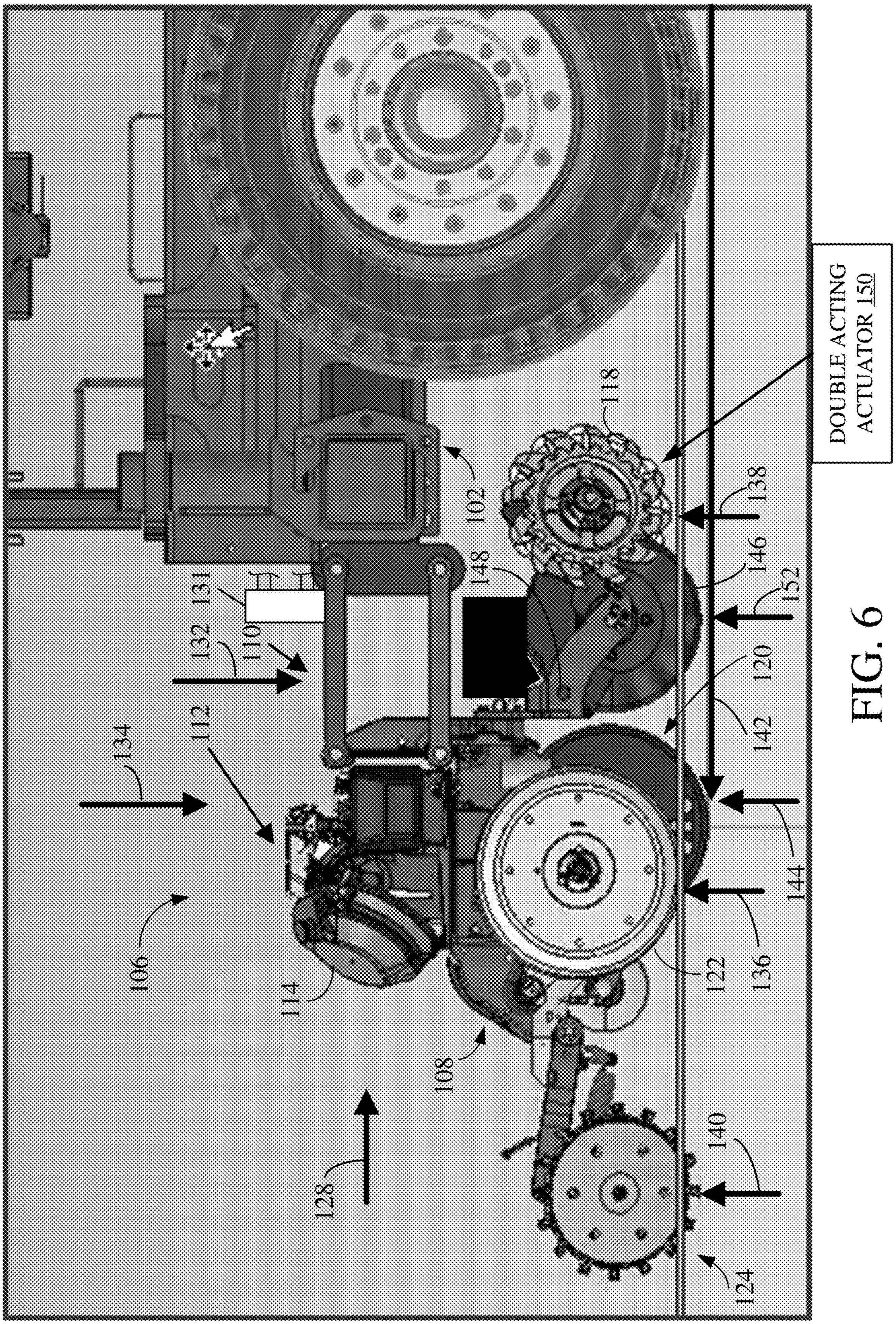

FIG. 6 is a side view showing another example of row unit 106 which is similar to FIG. 5, and similar items are similarly numbered. However, FIG. 6 shows that row unit 106 includes a colter 146. Colter 146 can be rigidly or movably coupled to frame 108. Also, in FIG. 6, row cleaner 118 is rotatably coupled to frame 108 at pivot axis 148. A double acting actuator 150 is coupled to frame 108 and to row cleaner 118 to controllably exert downforce and/or upforce on row cleaner 118 so that row cleaner 118 exerts more or less force on the ground ahead of opener 120. Similarly, FIG. 6 shows that the ground exerts an upward force on colter 146 when frame 108 is lowered so colter 146 penetrates the ground. The upward force on colter 146 is indicated by arrow 152. When a colter is used, then an indicator of soil strength can be calculated as follows:

$$\text{SoilStrength}=\text{RUDF}+\text{SelfWeight}-\text{GWReactionForce}-\text{DraftF}-\text{CWF}-\text{RCF}-\text{ColtF} \quad \text{EQ. 5}$$

where ColtF is the force 152 exerted on colter 146 by the ground.

Figure 7:
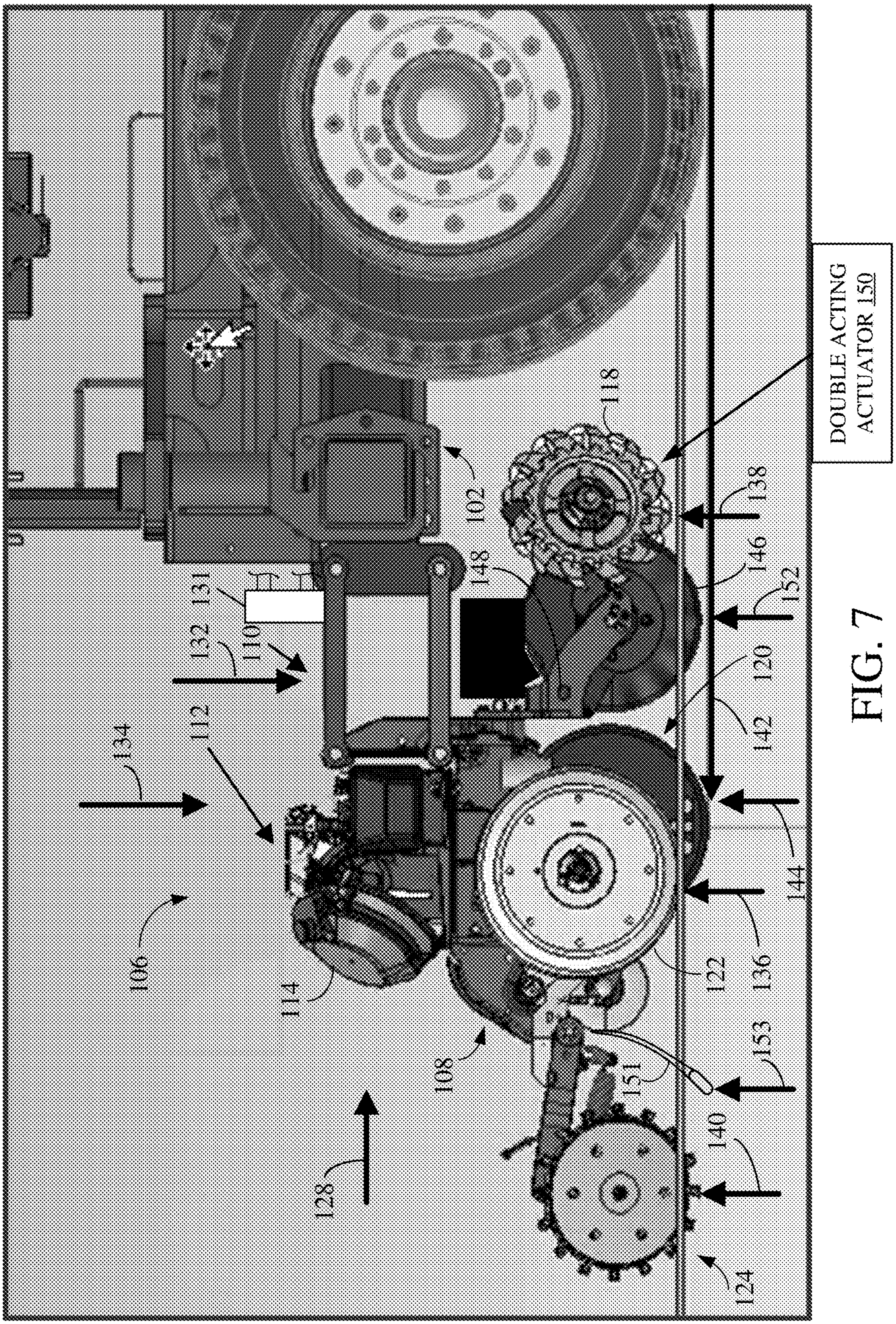

FIG. 7 is similar to FIG. 6 and similar items are similarly numbered. FIG. 7 shows that a seed firmer 151 may also be used to firm the seed within the furrow opened by opener 120. In such a case, the ground exerts an upward force on the seed firmer 151, as indicated by arrow 153. Therefore, the indicator of soil strength can be calculated as follows:

$$\text{SoilStrength}=\text{RUDF}+\text{SelfWeight}-\text{GWReactionForce}-\text{DraftF}-\text{CWF}-\text{RCF}-\text{ColtF}-\text{SFForce} \quad \text{EQ. 6}$$

where SFForce is the upwardly directed force on the seed firmer 151 as indicated by arrow 153.

Figure 8:
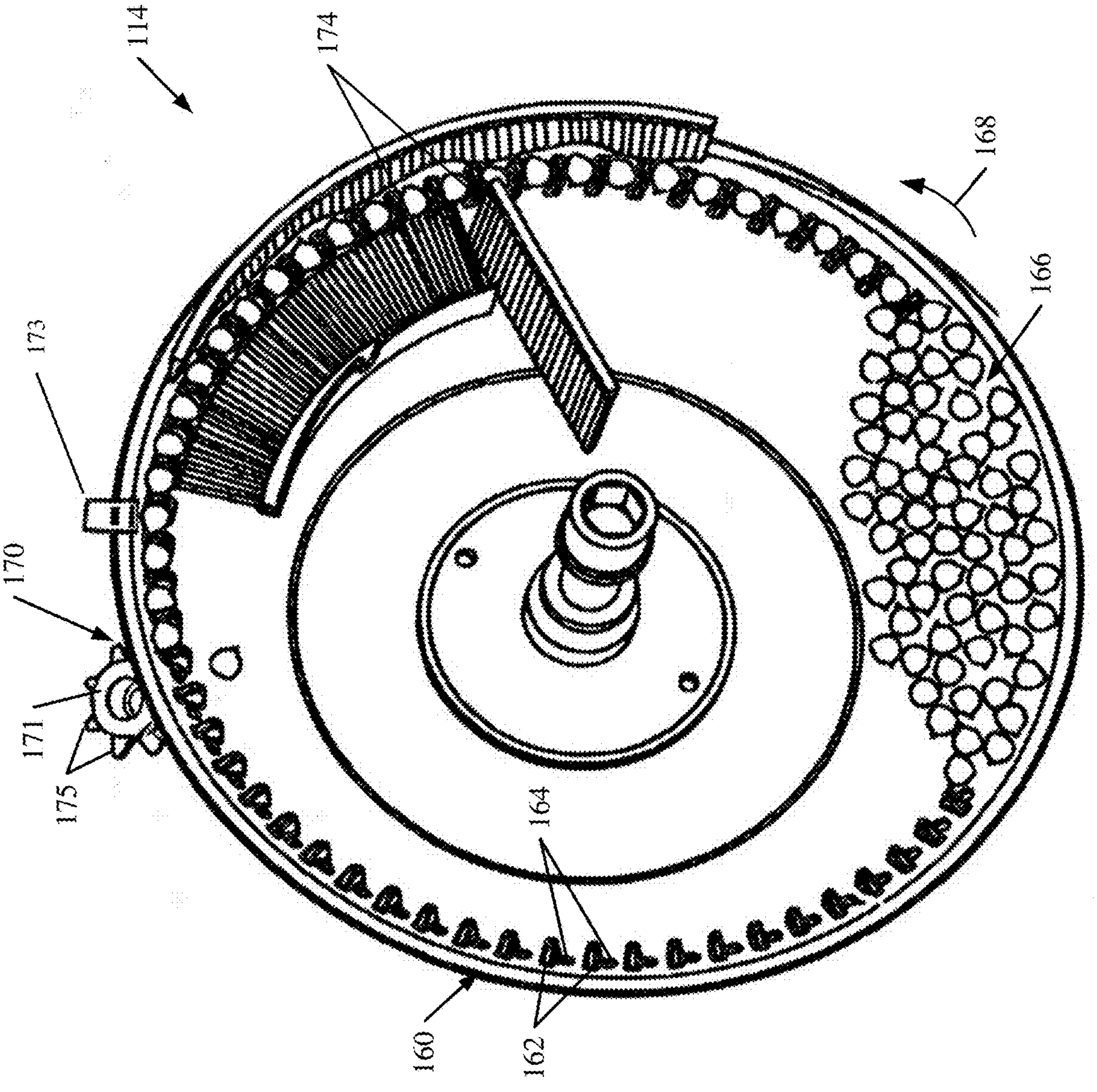
FIG. 8 is a perspective view of a portion of a seed metering system.
Figure 9:
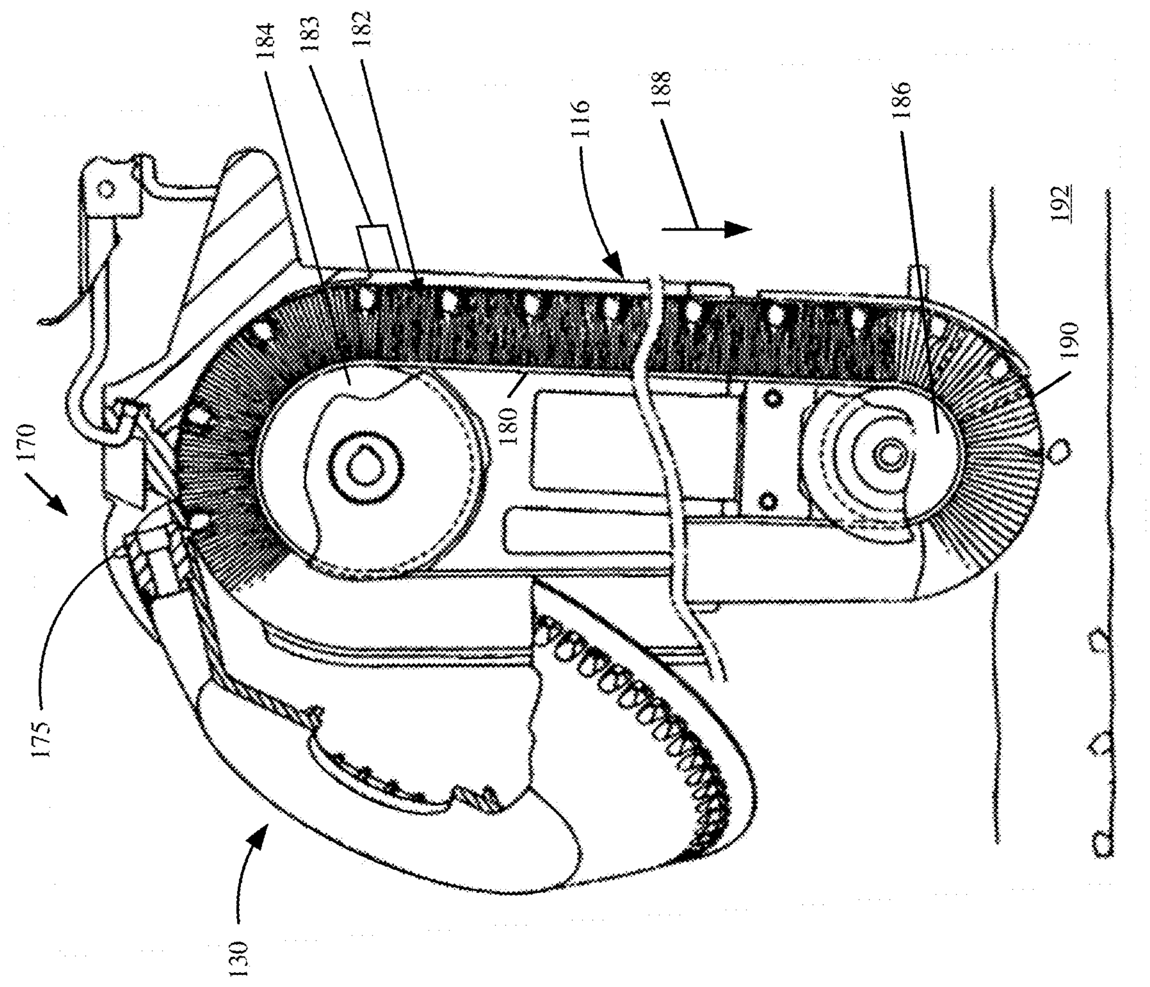
FIG. 9 shows one example of a seed delivery system that can be used with a seed metering system.

The present description describes a system that measures an indicator of soil strength, during operation of the row unit 106 and generates an action signal based on the indicator of soil strength. Before describing a system that controls downforce/upforce and generates other action signals based on soil strength, a description of one example of seed metering system 114 and seed delivery system 116 is first provided. FIGS. 8 and 9 show examples of metering system 114 and delivery system 116 in more detail. These are only examples of metering and delivery systems, and others can be used as well.

FIG. 8 shows one example of a rotatable mechanism 160 that can be used as part of the seed metering system 114. The rotatable mechanism 160 includes a rotatable disc, or concave element. Rotatable mechanism 160 has a cover (not shown) and is rotatably mounted relative to the frame 108 of the row unit 106. Rotatable mechanism 160 is driven by a motor and has a plurality of projections or tabs 162 that are closely proximate corresponding apertures 164. A seed pool 166 is disposed generally in a lower portion of an enclosure formed by rotatable mechanism 160 and its corresponding cover. Mechanism 160 is rotatably driven by its motor (such as an electric motor, a pneumatic motor, a hydraulic motor, etc.) for rotation generally in the direction indicated by arrow 168, about an axis. A pressure differential is introduced into the interior of the metering mechanism so that the pressure differential influences seeds from seed pool 166 to be drawn to apertures 164. For instance, a vacuum can be applied to draw the seeds from seed pool 166 so that they come to rest in apertures 164, where the vacuum holds them in place. Alternatively, a positive pressure can be introduced into the interior of the metering mechanism to create a pressure differential across apertures 164 to perform the same function.

Once a seed comes to rest in (or proximate) an aperture 164, the vacuum or positive pressure differential acts to hold the seed within the aperture 164 such that the seed is carried upwardly generally in the direction indicated by arrow 168, from seed pool 166, to a seed discharge area 170. It may happen that multiple seeds are residing in an individual seed cell. In that case, a set of brushes or other members 174 that are located closely adjacent the rotating seed cells tend to remove the multiple seeds so that only a single seed is carried by each individual cell. Additionally, a sensor 173 is also illustratively mounted adjacent to rotating mechanism 160.

Once the seeds reach the seed discharge area 170, a positive seed removal wheel, knock-out wheel 171, can act to remove the seed from the seed cell. Wheel 171 illustratively has a set of projections 175 that protrude at least partially into apertures 164 to actively dislodge the seed from those apertures. When the seed is dislodged, the seed is illustratively moved by the seed delivery system 116 to the furrow in the ground. The vacuum or pressure differential may be removed at some point as well.

FIG. 9 shows an example where the rotating element 160 is positioned so that its seed discharge area 170 is above, and closely proximate, seed delivery system 116 which includes a seed transport mechanism. In the example shown in FIG. 9, the seed transport mechanism includes a belt 180 with a brush that is formed of distally extending bristles 182 attached to belt 180. Belt 180 is mounted about pulleys 184 and 186. One of pulleys 184 and 186 is illustratively a drive pulley while the other is illustratively an idler pulley. The drive pulley is illustratively rotatably driven by a conveyance motor which can be an electric motor, a pneumatic motor, a hydraulic motor, etc. Belt 180 is driven generally in the direction indicated by arrow 188.

Therefore, when seeds are moved by rotating element 160 to the seed discharge area 170, where the seeds are discharged from the seed cells in rotating mechanism 160, the seeds are illustratively positioned within the bristles (e.g., in a receiver) 182 by the projections 162 following each aperture that pushes the seed into the bristles. Seed delivery system 116 includes walls that form an enclosure around the bristles, so that, as the bristles move in the direction indicated by arrow 188, the seeds are carried along with the bristles from the seed discharge area 170 of the metering mechanism, to a discharge area 190 at or near the furrow that is generated by the furrow opener 120 on the row unit 106.

Additionally, a sensor 183 is also illustratively coupled to seed delivery system 116. As the seeds are moved within bristles 182, sensor 183 can detect the presence or absence of a seed. It should also be noted that while the present description will proceed as having seed sensors 173 and 183, it is expressly contemplated that, in another example, only one seed sensor is used. Additional seed sensors can also be used.

In another example, seed delivery system 116 is not formed by a belt with distally extending bristles. Instead, the transport mechanism includes a flighted belt in which a set of paddles form individual chambers (or receivers), into which the seeds are dropped, from the seed discharge area 170 of the metering mechanism. The flighted belt moves the seeds from the seed discharge area 170 to the discharge area 190 within the trench or furrow 192.

There are a wide variety of other types of delivery systems as well, that include a transport mechanism and a receiver that receives a seed. For instance, the delivery system can include dual belt delivery systems in which opposing belts receive, hold and move seeds to the furrow, a rotatable wheel that has sprockets which catch seeds from the metering system and move the seed to the furrow, multiple transport wheels that operate to transport the seed to the furrow, an auger, among others. The present description will proceed with respect to a brush belt, but many other delivery systems are contemplated herein as well.

The present description provides a processing and control system for an agricultural machine that is configured to sense and/or calculate an indicator of soil strength and generate an action signal to control the planting machine based on the indicator of soil strength. The action signal may be used to communicate the soil strength to a mapping system that maps the soil strength. The action signal may be used to control the row unit or to control one or more machines during subsequent operations and/or to control other items.

Figure 10:
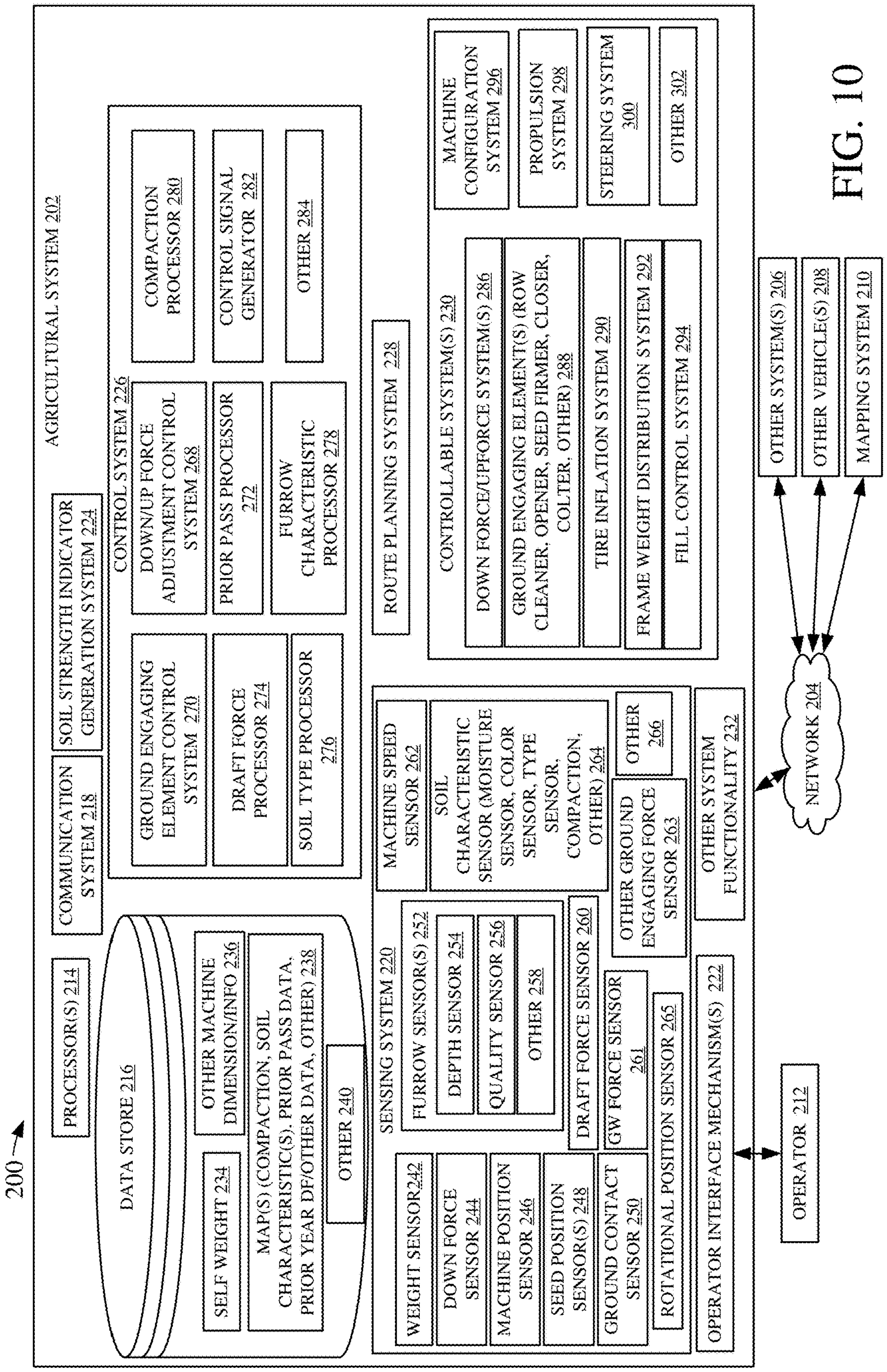
FIG. 10 is a simplified block diagram of one example of an agricultural machine architecture.

FIG. 10 is a block diagram of an agricultural machine architecture 200 in which agricultural system 202 can be disposed on a towing vehicle, on a towed implement 100, or on an individual row unit 106. Similarly, some items of agricultural system 202 can be used on the towing vehicle while other items are on the row unit 106 or on towed implement 100. The items in agricultural system 202 can be deployed in other ways as well. Further, some items of agricultural system 202 may be located on a remote server (e.g., in the cloud) as well, and the present processing and control system may be used on a manually operated machine, or on a semi-autonomous or fully autonomous machine.

In the example shown in FIG. 10, agricultural system 202 is shown as being able to communicate over network 204 with other systems 206, other vehicles 208, and mapping system 210. Also, FIG. 10 shows that an operator 212 can interact with agricultural system 202. Network 204 may be a wide area network, a local area network, a near field communication network, a cellular network, or any of a variety of other networks or combinations of networks. Other systems 206 can include farm manager systems, cloud-based systems, vendor systems, supplier systems, etc. Other vehicles 208 can include other vehicles operating in a same field, vehicles operating in other fields, vehicles performing subsequent operations in the field, or other vehicles. Mapping system 210 may be a mapping system that receives information from agricultural system 202 (such as soil strength values corresponding to different geographic locations) and generates a map using that information.

In the example shown in FIG. 10, agricultural system 202 includes one or more processors or servers 214, data store 216, communication system 218, sensing system 220, operator interface mechanisms 222, soil strength indicator generation system 224, control system 226, route planning system 228, controllable systems 230, and other system functionality 232. Data store 216 can include a self-weight measure 234 indicative of the self-weight of a particular row unit 106 or of a set of row units, as well as other machine dimensions or machine-specific information 236. Data store 216 can include maps 238 which may be compaction maps, maps of soil characteristics, prior pass information indicative of information used or generated (such as sensor signals or control signals) during one or more prior passes, prior year downforce information or soil strength maps, or maps of other settings used as locations during prior years, or other maps. Data store 216 can also include other information 240, such as code or other information, used to implement the functionality described herein.

Sensing system 220 includes weight sensor 242, downforce sensor 244, machine position sensor 246, seed position sensor 248 (which may be the seed sensors 153 and/or 173, along with machine speed sensors or other sensors that indicate seed position), ground contact sensor 250, furrow sensors 252 (which may include depth sensor 254, quality sensor 256, and other sensors 258), draft force sensor 260, gage wheel sensor 261, other force sensor 263, machine speed sensor 262, one or more soil characteristic sensors 264, and other types of sensors 266. Control system 226 can include downforce/upforce adjustment control system 268, ground-engaging element control system 270, prior pass processor 272, draft force processor 274, soil type processor 276, furrow characteristic processor 278, compaction processor 280, control signal generator 282, and other items 284. Controllable systems 230 can include downforce/upforce systems 286, ground-engaging elements 288 (which may include a row cleaner, a furrow opener, a seed firmer, a closer, a colter, a fertilizer opener, or other ground-engaging elements), tire inflation system 290, frame weight distribution system 292, fill control system 294, machine configuration system 296, propulsion system 298, steering system 300, and other items 302.

Before describing the overall operation of architecture 200 in more detail, a description of some of the items in architecture 200 and their operation, will first be provided.

Communication system 218 facilitates communication of the items of system 200 with one another and may facilitate communication over network 204. Therefore, communication system 218 may include a controller area network (CAN) bus and bus controller, and other communication functionality may depend on the type of network 204 over which communication system 218 is to communicate.

Weight sensor 242 may be a scale, or other sensor that senses the weight of a row unit 106 or a set of row units. The weight of the row unit may be already known as self-weight 234 in data store 216. However, depending on the type of hoppers that row unit 106 includes, that weight may vary during operation. Therefore, weight sensor 242 may provide a real time indication of the weight of row unit 106 or a set of row units. As an example, when the row unit 106 is lifted out of the ground, the weight may be detected. Downforce sensor 244 illustratively senses the downforce and/or upforce generated by the row unit downforce/upforce generator 131. Downforce sensor 244 may be a strain gauge, a scale, or another sensor that senses the row unit downforce and/or upforce. Machine position sensor 246 may be a global navigation satellite system (GNSS) receiver, a dead reckoning system, a cellular triangular system, or another system that detects the location of row unit 106 in a global or local coordinate system. Seed position sensor 248 may include the seed sensors discussed above and/or additional information that identifies the position of the seed within the metering system or delivery system, or the position of the seed in the furrow. Ground contact sensor 250 generates an output indicative of whether row unit 106 is coming out of contact with the ground. For instance, an accelerometer or an inertial measurement unit or other sensor that senses the ride quality of row unit 106 may provide an output indicating that row unit 106 is bouncing out of the ground or is otherwise losing contact with the ground. Also, a gage wheel position sensor or a value derived from a downforce sensor may be used to sense when row unit 106 is coming out of contact with the ground. For instance, if the gage wheels 122 are in the fully lowered position and/or when a downforce sensor indicates that there is no downforce, this may indicate that the gage wheel 122 and/or row unit are not in firm contact with the ground.

Furrow sensors 252 can include optical sensors, other touchless or noncontact sensors such as radar, infrared sensors, etc.), or other sensors that sense the depth of the furrow being created by furrow opener 120 and the quality of the furrow. As another example, depth sensor 254 may be a sensor that senses the relative position of gage wheel 122 relative to furrow opener 120 on frame 108 to obtain an indication of the depth of the furrow being opened by furrow opener 120. Quality sensor 256 may be an optical sensor that senses whether the sides of the furrow are smearing or cracking, whether the sides of the furrow are crumbling, or other information indicative of the quality of the furrow being opened by furrow opener 120.

Draft force sensor 260 illustratively senses the draft force needed to pull row unit 106 through the soil. The draft force sensor may be located on tool bar 102 to sense the draw weight or draw force on tool bar 102 corresponding to a row unit 106 or a set of row units 106. Draft force sensor 260 can take other forms as well. Gage wheel sensor 261 senses the gage wheel reaction force discussed above with respect to equations 1-6. Other force sensor 263 senses the force of the ground on the other soil engaging elements of row unit 106, such as the row cleaner 118, colter 146, a seed firmer, closing wheels 124, the draft force, etc. Rotational position sensor 265 senses the rotational position of row unit 106 about its connection point(s) to tool bar 102 and can be a potentiometer, Hall Effect sensor, etc. Machine speed sensor 262 illustratively generates an output indicative of the ground speed of row unit 106 or a set of row units 106 or of the towing vehicle. Machine speed sensor 262 may also derive the machine speed from other sensor inputs. For instance, machine speed sensor 262 may be logic that receives multiple outputs from machine position sensor 246 and identifies the machine speed, and direction of travel, based upon those multiple outputs. Soil characteristic sensor 264 can be one or more sensors that sense characteristics of the soil in the furrow being generated by furrow opener 120. The sensors 264 can be optical sensors, capacitive sensors, or other sensors that may sense soil characteristics such as soil moisture, soil color, soil type, etc.

Operator interface mechanisms 222 may be located on the towing vehicle that is towing towed implement 100 or in a remote device that can be used remotely regardless of whether the planting machine is operating autonomously. The operator interface mechanisms 222 may include a steering wheel, joysticks, levers, buttons, dials, pedals, or other mechanisms. In addition, the operator interface mechanisms 222 can include mechanisms for providing audio, visual and/or haptic outputs and receiving operator inputs. Such mechanisms can include a display screen or touch sensitive display screen that displays information to the operator as well as actuatable mechanisms that can be actuated by the operator to provide operator inputs. The actuatable mechanisms may include such things as links, icons, buttons, drop down menus, or other mechanisms that can be actuated using a point and click device, using voice control commands, using touch gestures, etc.

Soil strength indicator generation system 224 receives inputs from sensing system 220, and may receive other inputs (such as from data store 216 or other inputs such as the momentary force that is being generated by down/up force adjustment control system 268 which may result in outputs from sensing system 220), and generates a soil strength indicator that has a value indicative of the strength of the soil over which row unit 106 is traveling. In one example, for instance, soil strength indicator generation system 224 receives sensor inputs indicative of the variables in one or more of equations 1-6 set out above and generates a soil strength indicator value based upon those variable values. Soil strength indicator generation system 224 generates an output indicative of the soil strength indicator value and provides that output to control system 226 which generates one or more action signals or control signals based upon the soil strength indicator value.

Control system 226 can aggregate a plurality of different soil strength indicator values received from soil strength indicator generation system 224 to identify a predictive value of soil strength for the soil that row unit 106 is approaching as well. Down/up force adjustment control system 268 can generate an output indicative of how the downforce or upforce should be adjusted on row unit 106 based upon the soil strength indicator or based upon a collection or aggregated set of soil strength indicators. Ground engaging element control system 270 can generate an output indicative of how the downforce/upforce applied to other ground engaging elements (such as row cleaner 118, colter 146, furrow closer 124, seed firmer 151, or other ground engaging element) is to be adjusted based upon the soil strength output from system 224. Prior pass processor 272 can receive information (such as from data store 216 or data from another machine or vehicle 208) which is indicative of a value encountered during a prior pass at the current location or adjacent the current location of row unit 106. For instance, if, on the prior pass at the location adjacent the current location of row unit 106, the soil type was identified as sandy soil and a particular downforce adjustment was made to maintain the furrow at a constant depth, that information may be stored in data store 216 and prior pass processor 272 may receive that information, along with the current soil strength output from system 224, and generate an output indicative of an action that should be taken based upon the information from the prior pass.

Draft force processor 274 can calculate the rotational force, and the upward component of the draft force, and/or rotational position of row unit 106 and/or rotational position of the other components on row unit 106 based on an output from sensor 265, based on the output from draft force sensor 260, based on the speed of the row unit 106, and/or based on other information. The output from processor 274 can be used by soil strength indicator generation system 224 in its generation of the soil strength indicator value, or the output from processor 274 can be applied, to the output of soil strength indicator generation system 224 to account for the upward component of the draft force on row unit 106. Furrow characteristic processor 278 can receive an output from furrow sensors 254 as well as the output from soil strength indicator generation system 224 and other items, to generate an output indicative of an action signal or adjustment signal to be generated based upon the current quality of the furrow being generated by furrow opener 120. By way of example, if the gage wheels 122 are exerting excess compaction force, or too little compaction force, these things may be identified by analyzing the furrow quality. Soil type processor 276 may receive inputs from soil characteristic sensors 264 and generate an output indicative of the soil type of soil over which row unit 106 is traveling. Compaction processor 280 can process compaction information such as information from compaction maps and information indicative of where different machines have traveled under different conditions (e.g., row unit 106 can compact the soil to a greater degree as the machine travels over it, if the soil is wet). Compaction processor 280 can use a current soil strength value and estimate compaction or soil strength after the machine travels over the ground and exerts additional compaction on the soil, thus increasing the soil strength. Compaction processor 280 can generate other compaction indicators as well, in addition to soil strength. Compaction processor 280 generates an output indicative of an action signal that should be generated based upon the compaction information.

Control signal generator 282 is illustratively configured to receive the information from the other processors and systems in control system 226 (and possibly other items) and generate an output indictive of one or more actions or control signals based upon those inputs. Control signal generator 282 may be one or more classifiers, machine learned models, or a deep learning system that receives inputs and generates an output indicative of one or more actions that should be taken based on those inputs, a rules-based system, or any of a wide variety of other systems that receive inputs and generate an output indicative of a control signal or action based on the inputs.

Route planning system 228 may receive inputs from the various other items in system 212 and generate a route for the towing vehicle that is towing implement 100, or for other vehicles based upon the received information. For instance, route planning system 228 may receive inputs indicating that the soil is moist in certain areas of the field and is dry in other areas of the field. In that case, it may be that greater downforce is needed in the dry areas while less downforce is needed in the wet areas. Thus, route planning system 228 can generate an output that, when followed, navigates the towing vehicle to the dry areas when the seed hoppers or other containment vessels on the towed implement 100 are more full (and thus heavier) and navigates the towing vehicle to move to the wetter areas (where less downforce is needed) when the tanks or other containment vessels are less full (and thus lighter).

The control signal generator 282 can generate control signals to control one or more of the controllable systems 230, or other controllable systems.

Downforce/upforce systems 286 can include one or more of the row unit downforce/upforce generators 131 on towed implement 100. Generators 131 can be controlled in groups of row units) or individually for individual row units. System 286 can also include double acting actuator 150 and other elements that generate downforce and/or upforce on the ground engaging elements 288 of row unit 106, or a set of row units 106.

Therefore, in one example, control signal generator 282 can consider the depth and quality of the furrow, along with the soil strength indicator, and characteristics of the closing wheels 124 (such as whether closing wheels 124 are blades or wider wheels, whether they are rubber, cast iron, smooth, or spiked, etc.) to determine how much downforce or upforce to exert on the closing wheels 124. In another example, a wide variety of factors (such as soil characteristics—e.g., soil type and soil moisture) can be considered along with the soil strength indicator to determine how much downforce or upforce to exert on speed firmer 151, colter 146, row cleaner 118, or other ground engaging elements on row unit 106. Once the downforce or upforce on any ground engaging element is adjusted, this may mean that the row unit downforce or upforce, or the downforce or upforce exerted on other ground engaging elements on row unit 106, should be re-adjusted. These are examples only, and it may be that, for instance, only downforce is adjusted on the row unit and/or ground engaging elements.

Tire inflation system 290 can be controlled to vary the inflation pressure of the tires on towed implement 100, on the towing vehicle, etc. For instance, where the soil strength is relatively low, the tires may be deflated to increase the contact patch between those tires and the soil and thus reduce the amount of compaction on the soil. Where the soil strength is relatively high, the tires may be inflated more to increase fuel efficiency.

Frame weight distribution system 292 can include a controllable system that moves weight around the frame of the towed implement 100 to redistribute the weight on implement 100. For instance, where the downforce on row units located more toward the center of towed implement 100 is to be higher, then weight may be redistributed in order to facilitate higher downforce at the row units on the center of the towed implement while avoiding smiling (where the row units on the outside edges of the towed implement are lifted out of contact with the ground). The frame weight distribution system 292 may be a hydraulic, electric, or other system that distributes weight about the frame of the towed implement.

Fill control system 294 may be a system that controls how much material (seed, nutrients, etc.), is loaded into the hoppers or containment vessels on towed implement 100. Where towed implement 100 is going to be traveling over soil with a relatively low soil strength, then the filling operation may be controlled so that less material is loaded into the tanks, hoppers, or other containment vessels until towed implement 100 is traveling over higher strength soil.

Machine configuration system 296 may be used to control the configuration of elements on row unit 106 or towed implement 100. Such elements may include adjusting the spring strength of suspension springs or other springs on implement 100, changing the angle of engagement of the furrow opener, the colter, or other soil engaging elements, or other machine configuration settings.

Propulsion system 298 illustratively includes an engine and transmission (or individual motors for different wheels) or other systems for driving ground engaging elements (e.g., wheels or tracks) of towed implement 100 or the towing vehicle or both. By way of example, where limited downforce is available, control signal generator 282 may control propulsion system 298 to slow down the ground speed of the row unit 106 so that sufficient downforce is available to obtain desired planting operation (e.g., to obtain the desired furrow depth, furrow quality, etc.).

Steering system 300 may be controlled to steer the direction or heading of the towing implement or the planting machine where the planting machine is a self-propelled vehicle. The steering system 300 can be controlled to navigate the towing vehicle along a route so that the row units 106 can obtain adequate planting performance.

Figure 11:
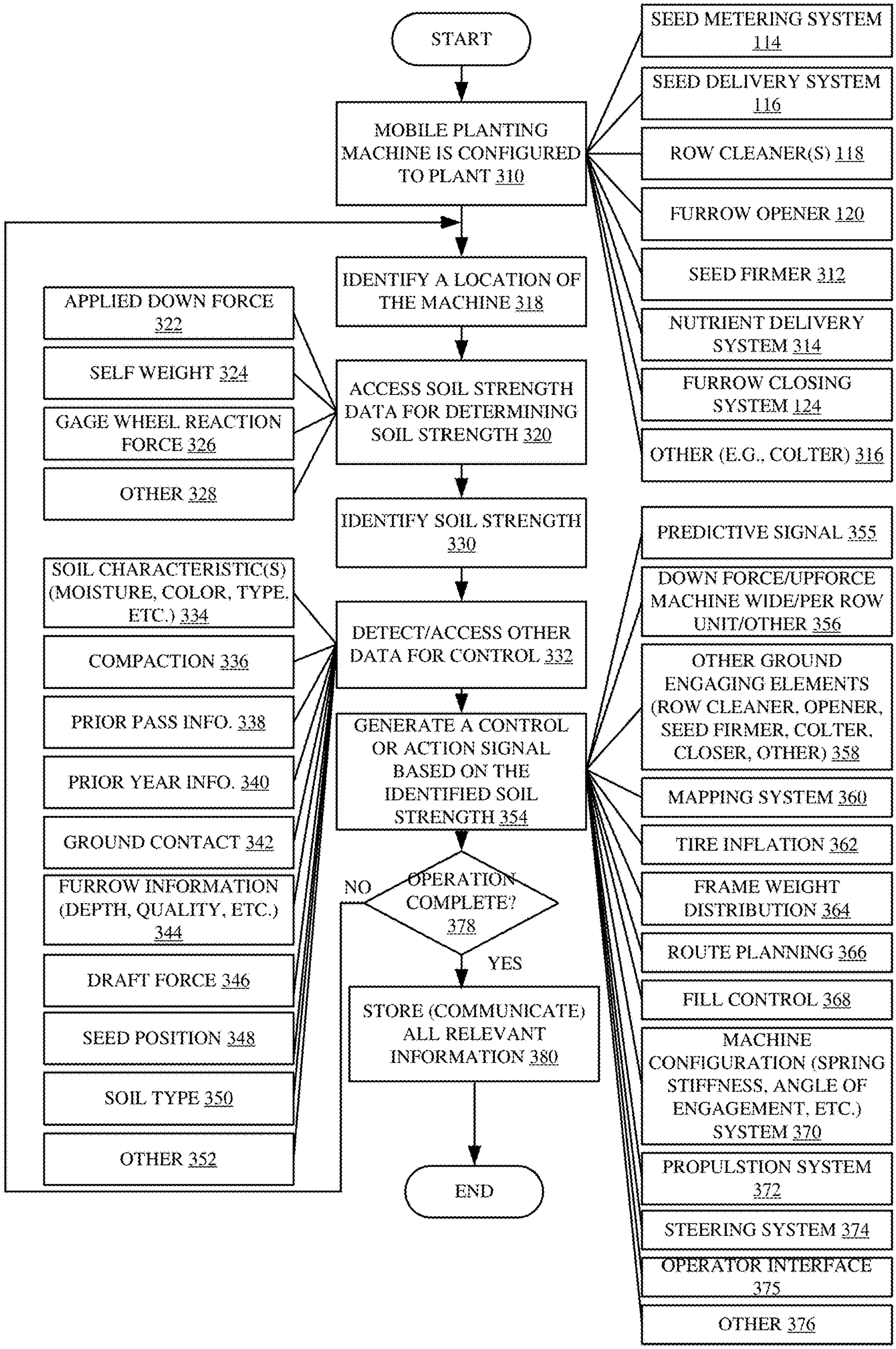
FIG. 11 is a flow diagram of one example operation of an agricultural system.

FIG. 11 is a flow diagram illustrating one example of the operation of architecture 200 in more detail. A mobile planting machine is configured to perform a planting operation in a field, as indicated by block 310 in the flow diagram of FIG. 11. In one example, the planting machine is a row unit 106 that is towed by a towing vehicle and has a seed metering system 114, a seed delivery system 116, one or more row cleaners 118, a furrow opener 120, a seed firmer 312, a nutrient delivery system 314 (which can deliver nutrients or other material), furrow closing system 124, and it can include other items 316. At some point, machine position sensor 246 detects a location of the machine as indicated by block 318. Soil strength indicator generation system 224 accesses soil strength data for determining the value of a soil strength indicator, indicative of the strength of the soil over which row unit 106 is traveling, or has traveled. Accessing the soil strength information is indicated by block 320. The soil strength information can include the applied downforce 322 (referred to in Equations 1-6 above as the RUDF variable) from downforce sensor 244 and the weight of the row unit 324, indicated in the above equations as the SelfWeight, from weight sensor 242 or data store 216. The soil strength data can also include the gage wheel reaction force 326 identified in the above equations as the GWReactionForce variable generated by gage wheel sensor 261. The soil strength data can also include other information 328, some of which is described above with respect to Equations 1-6. Soil strength indicator generation system 224 then identifies the soil strength indicator, as indicated by block 330. The soil strength can be identified using any of the Equations 1-6 discussed above, or other equations, to obtain an indicator value indicative of soil strength.

The soil strength indicator value is output from system 224 to control system 226. Control system 226 detects or accesses other data in order for control signal generator 282 to generate an action signal or other control signal based upon the value of the soil strength indicator. Detecting or accessing the other data in order to generate a control signal or action signal is indicated by block 332 in the flow diagram of FIG. 11.

For instance, control system 226 can detect or access the soil characteristics sensed by sensor(s) 264 (such as soil moisture, soil color, soil type, etc.) as indicated by block 334. The compaction processor 280 can obtain compaction information 336. Prior pass processor 272 can obtain prior pass information 338. Prior pass processor 272 can also obtain information from passes made during prior years, as indicated by block 340. Control signal generator 282 can obtain information indicative of whether row units 106 are losing ground contact and/or how much reaction force they are experiencing from the ground due to blades fully penetrating to proper depth as a function of applied downforce, as indicated by block 342. Furrow characteristic processor 278 can obtain furrow information, such as information indicative of furrow depth, furrow quality, etc., as indicated by block 344. Draft force processor 274 can obtain information indicative of the draft force, an upward component of the draft force, or rotational force being exerted on row unit 106, as indicated by block 346. Control signal generator 282 can also obtain information from seed position sensor 248 indicative of the seed position, as indicated by block 348. Soil type processor 276 can obtain information from soil characteristic sensors 264 indicative of soil type, as indicated by block 350. Control signal generator 282 can obtain or detect any of a wide variety of other information as well, as indicated by block 352.

Based upon the soil strength data and any of the information obtained or accessed by control signal generator 282, control signal generator 282 generates one or more control signals (also referred to as action signals) as indicated by block 354 in the flow diagram of FIG. 11. The control signals can be predictive control signals 355 that will be used in the future as the row unit travels through the field. The control signals can be downforce/upforce control signals to control the downforce/upforce systems 286 on a per row unit basis, or for a set of row units, or on a machine wide basis as indicated by block 356. The control signals or action signals can be used to control other ground engaging elements 288 (such as the downforce or upforce on the row cleaner, the colter, the closing wheel, the seed firmer, etc.), as indicated by block 358. The control signal or action signal can be provided to mapping system 210 so mapping system 210 can map the soil strength indicator and other information generated by control system 226 to the geographic locations in the field, as indicated by block 360 in FIG. 11. Such mapped values can be used in subsequent passes, for predicting harvest or other operation settings, and/or for assisting in identifying initial settings for subsequent planting or other operations. The control signal generated by control signal generator 282 can be used to control tire inflation system 290, as indicated by block 362. The control signal can be generated to control frame weight distribution system 292, as indicated by block 364. The control signal can be output to route planning system 228 to control route planning, as indicated by block 366. The control signal can be generated to control fill control system 294 to control the fill level of the various containment vessels on row unit 106 or a set of row units 106, as indicated by block 368. The control signal can be generated to control machine configuration system 296 to control machine configurations such as spring stiffnesses, angle of engagement, and other items, as indicated by block 370 in FIG. 11. The control signal can be used to control propulsion system 298 in order to control the speed of row unit 106 or of the towing vehicle, as indicated by block 372. The control signal can be used to control steering system 300, in order to control the route or direction of travel of the towing vehicle, as indicated by block 372. The control signal can be generated to control operator interface mechanisms 222 to output the soil strength indicator to operator 212, as indicated by block 375 or to control communication system 218 to send the soil strength indicator to other systems 206 or other vehicle 208 or to control a wide variety of other items based on soil strength and other information, as indicated by block 376.

Until the operation is complete, as indicated by block 378, processing may revert to block 318 where the location of the row unit 106 is updated and the soil strength is again evaluated at that location, etc. Once the operation is complete, as indicated by block 378, then control signal generator 282 can be used to control communication system 218 to store all of the information generated during the operation (or a subset of that information) either locally on data store 216 or remotely on other systems 206 or both locally and remotely. Similarly, some information can be stored locally while other information is stored remotely, as well. Storing all of the relevant information is indicated by block 380 in the flow diagram of FIG. 11.

It can thus be seen that the present description describes a system which generates an output, on the fly, during the planting operation, indicative of soil strength. The soil strength information can be used to generate other information and/or to generate any of a wide variety of control signals or action signals.

It will be noted that the above discussion has described a variety of different systems, components, processors, generators, and/or logic. It will be appreciated that such systems, components, processors, generators, and/or logic can be comprised of hardware items (such as processors and associated memory, or other processing components, some of which are described below) that perform the functions associated with those systems, components, processors, generators, and/or logic. In addition, the systems, components and/or logic can be comprised of software that is loaded into a memory and is subsequently executed by a processor or server, or other computing component, as described below. The systems, components, processors, generators, and/or logic can also be comprised of different combinations of hardware, software, firmware, etc., some examples of which are described below. These are only some examples of different structures that can be used to form the systems, components, processors, generators, and/or logic described above. Other structures can be used as well.

The present discussion has mentioned processors, processing systems, controllers and/or servers. In one example, these can include computer processors with associated memory and timing circuitry, not separately shown. They are functional parts of the systems or devices to which they belong and are activated by, and facilitate the functionality of the other components or items in those systems.

Also, a number of user interface (UI) displays have been discussed. The UI displays can take a wide variety of different forms and can have a wide variety of different user actuatable input mechanisms disposed thereon. For instance, the user actuatable input mechanisms can be text boxes, check boxes, icons, links, drop-down menus, search boxes, etc. The mechanisms can also be actuated in a wide variety of different ways. For instance, the mechanisms can be actuated using a point and click device (such as a track ball or mouse). The mechanisms can be actuated using hardware buttons, switches, a joystick or keyboard, thumb switches or thumb pads, etc. The mechanisms can also be actuated using a virtual keyboard or other virtual actuators. In addition, where the screen on which they are displayed is a touch sensitive screen, the mechanisms can be actuated using touch gestures. Also, where the device that displays them has speech recognition components, the mechanisms can be actuated using speech commands.

A number of data stores have also been discussed. It will be noted the data stores can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

Figure 12:
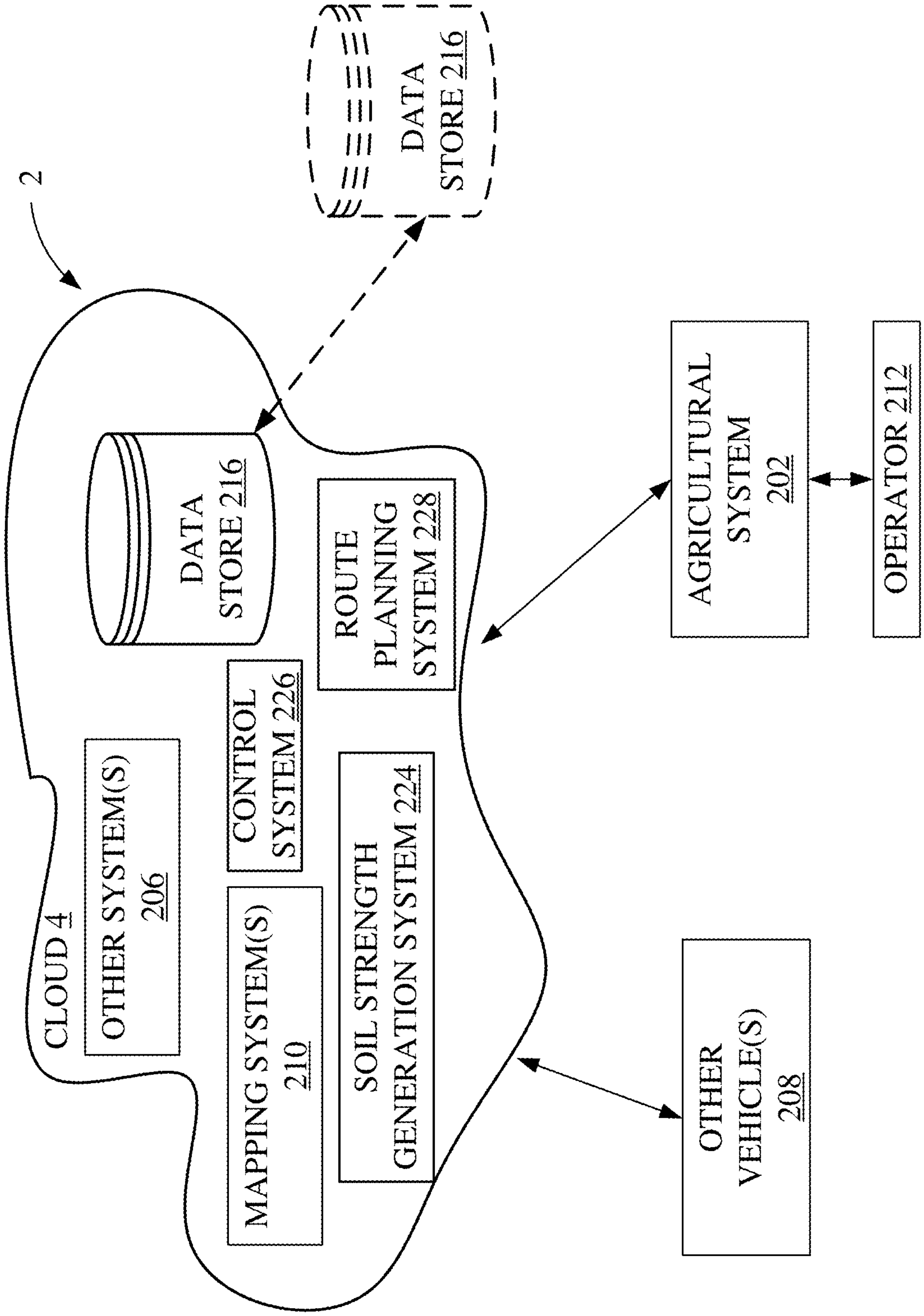
FIG. 12 is a block diagram showing one example of the architecture illustrated in FIG. 6, deployed in a remote server architecture.

FIG. 12 is a block diagram of one example of the agricultural machine architecture, shown in FIG. 10, where agricultural system 202 communicates with elements in a remote server architecture 2. In an example, remote server architecture 2 can provide computation, software, data access, and storage services that do not require end-user knowledge of the physical location or configuration of the system that delivers the services. In various examples, remote servers can deliver the services over a wide area network, such as the internet, using appropriate protocols. For instance, remote servers can deliver applications over a wide area network and they can be accessed through a web browser or any other computing component. Software or components shown in FIG. 10 as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the example shown in FIG. 12, some items are similar to those shown in FIG. 10 and they are similarly numbered. FIG. 12 specifically shows that control system 226, mapping system 210, and other systems 206 can be located at a remote server location 4. Therefore, agricultural system 202 accesses those systems through remote server location 4.

Regardless of where they are located, the items can be accessed directly by agricultural machine 202, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an example, where cell coverage is poor or nonexistent, another mobile machine (such as a fuel truck) can have an automated information collection system. As the agricultural machine comes close to the fuel truck for fueling, the system automatically collects the information from the machine or transfers information to the machine using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the agricultural machine until the agricultural machine enters a covered location. The agricultural machine, itself, can then send and receive the information to/from the main network.

It will also be noted that the elements of FIG. 10, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 13:
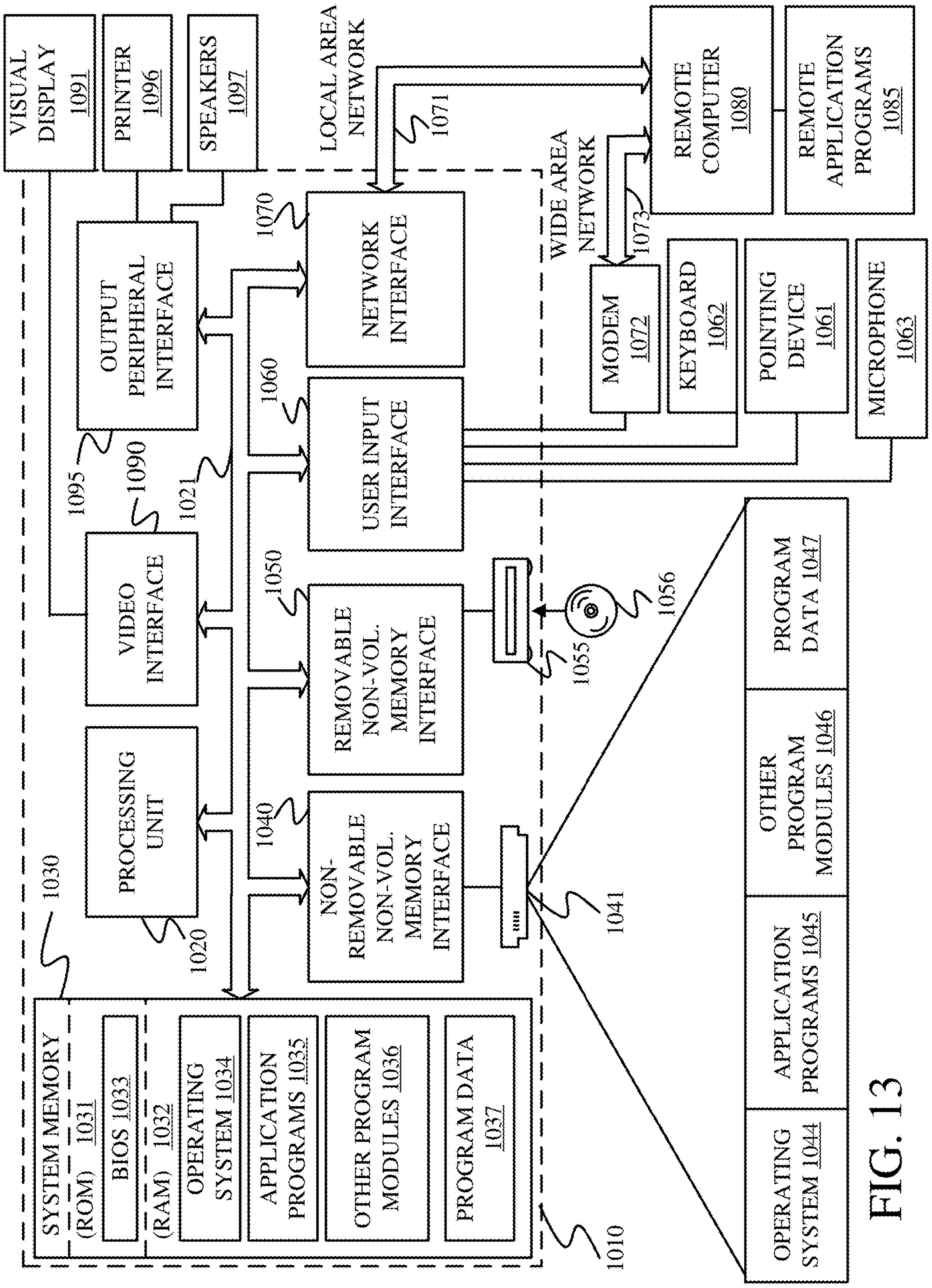
FIG. 13 is a block diagram showing one example of a computing environment that can be used in the architectures shown in the previous figures.

FIG. 13 is one example of a computing environment in which elements of FIG. 10, or parts of it, (for example) can be deployed. With reference to FIG. 13, an example system for implementing some embodiments includes a computing device in the form of a computer 1010. Components of computer 1010 may include, but are not limited to, a processing unit 1020 (which can comprise processors or servers from previous FIGURES), a system memory 1030, and a system bus 1021 that couples various system components including the system memory to the processing unit 1020. The system bus 1021 may be any of several types of bus structures including a memory bus or memory controller, a peripheral bus, and a local bus using any of a variety of bus architectures. Memory and programs described with respect to FIG. 10 can be deployed in corresponding portions of FIG. 13.

Computer 1010 typically includes a variety of computer readable media. Computer readable media can be any available media that can be accessed by computer 1010 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 1010. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 1030 includes computer storage media in the form of volatile and/or nonvolatile memory such as read only memory (ROM) 1031 and random access memory (RAM) 1032. A basic input/output system 1033 (BIOS), containing the basic routines that help to transfer information between elements within computer 1010, such as during start-up, is typically stored in ROM 1031. RAM 1032 typically contains data and/or program modules that are immediately accessible to and/or presently being operated on by processing unit 1020. By way of example, and not limitation, FIG. 13 illustrates operating system 1034, application programs 1035, other program modules 1036, and program data 1037.

The computer 1010 may also include other removable/non-removable volatile/nonvolatile computer storage media. By way of example only, FIG. 13 illustrates a hard disk drive 1041 that reads from or writes to non-removable, nonvolatile magnetic media, an optical disk drive 1055, and nonvolatile optical disk 1056. The hard disk drive 1041 is typically connected to the system bus 1021 through a non-removable memory interface such as interface 1040, and optical disk drive 1055 is typically connected to the system bus 1021 by a removable memory interface, such as interface 1050.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 13, provide storage of computer readable instructions, data structures, program modules and other data for the computer 1010. In FIG. 13, for example, hard disk drive 1041 is illustrated as storing operating system 1044, application programs 1045, other program modules 1046, and program data 1047. Note that these components can either be the same as or different from operating system 1034, application programs 1035, other program modules 1036, and program data 1037.

A user may enter commands and information into the computer 1010 through input devices such as a keyboard 1062, a microphone 1063, and a pointing device 1061, such as a mouse, trackball or touch pad. Other input devices (not shown) may include a joystick, game pad, satellite dish, scanner, or the like. These and other input devices are often connected to the processing unit 1020 through a user input interface 1060 that is coupled to the system bus, but may be connected by other interface and bus structures. A visual display 1091 or other type of display device is also connected to the system bus 1021 via an interface, such as a video interface 1090. In addition to the monitor, computers may also include other peripheral output devices such as speakers 1097 and printer 1096, which may be connected through an output peripheral interface 1095.

The computer 1010 is operated in a networked environment using logical connections (such as a local area network—LAN, or wide area network—WAN, or a controller area network—CAN) to one or more remote computers, such as a remote computer 1080.

When used in a LAN networking environment, the computer 1010 is connected to the LAN 1071 through a network interface or adapter 1070. When used in a WAN networking environment, the computer 1010 typically includes a modem 1072 or other means for establishing communications over the WAN 1073, such as the Internet. In a networked environment, program modules may be stored in a remote memory storage device. FIG. 13 illustrates, for example, that remote application programs 1085 can reside on remote computer 1080.

It should also be noted that the different examples described herein can be combined in different ways. That is, parts of one or more examples can be combined with parts of one or more other examples. All of this is contemplated herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer implemented method of controlling an agricultural machine comprising a row unit, the computer implemented method comprising:
- detecting a row unit down force (RUDF) applied to the row unit by a down force actuator;
- obtaining a weight value representing a self weight of the row unit;
- sensing, by a gage wheel reaction force sensor, a gage wheel reaction force imparted by ground on a gage wheel of the row unit;
- detecting a furrow depth indicative of a depth of a furrow opened by a furrow opener on the row unit;
- calculating a soil strength metric based on the detected furrow depth and a soil strength value comprising the difference between (i) a calculated sum of at least the RUDF and the self weight and (ii) at least the gage wheel reaction force,
  - wherein the soil strength value represents at least one of soil resistance or soil compaction; and
- controlling the agricultural machine based on the soil strength value.

2. The computer implemented method of claim 1, wherein the soil strength value comprising the difference between (i) the calculated sum of at least the RUDF and the self weight and (ii) a calculated sum of at least the gage wheel reaction force and an additional reaction force.

3. The computer implemented method of claim 2, and further comprising:
- detecting a force on a furrow closer on the row unit as a furrow closer force, wherein the additional reaction force includes the furrow closer force.

4. The computer implemented method of claim 2, and further comprising:
- detecting a force on a row cleaner on the row unit as a row cleaner force, wherein the additional reaction force includes the row cleaner force.

5. The computer implemented method of claim 2, and further comprising:
- detecting a rotational force exerted on the row unit by pulling the row unit with a towing vehicle, the rotational force having an upward component in a direction away from the ground, wherein the additional reaction force includes the rotational force.

6. The computer implemented method of claim 5 wherein detecting the rotational force comprises:
- detecting travel speed of the row unit; and
- detecting the rotational force based on the travel speed of the row unit.

7. The computer implemented method of claim 2, and further comprising:
- detecting a force on a colter wheel on the row unit as a colter wheel force, wherein the additional reaction force includes the colter wheel force.

8. The computer implemented method of claim 2, and further comprising:
- detecting a force on a seed firmer on the row unit as a seed firmer force, wherein the additional reaction force includes the seed firmer force.

9. The computer implemented method of claim 1, wherein the row unit includes a row unit frame supporting one or more row unit components, and the weight value represents at least a weight of the row unit frame.

10. The computer implemented method of claim 1, wherein obtaining the weight value representing the self weight of the row unit comprises detecting, by a self weight detector, a self weight measure representing the self weight of the row unit.

11. An agricultural system with a row unit including a row unit frame supporting at least one row unit component, the agricultural system comprising:
- a self weight detector configured to detect a self weight measure representing a self weight of the row unit, the self weight including at least the row unit frame;
- at least one processor; and
- a memory that stores computer executable instructions which, when executed by the at least one processor, causes the at least one processor to perform steps, comprising:
- lifting the row unit out of the ground;
- detecting, by the self weight detector, the self weight measure while the row unit is lifted;
- detecting a row unit down force applied to the row unit by a down force actuator;
- detecting a force imparted by ground on a gage wheel as a gage wheel reaction force;
- calculating a soil strength value based on the row unit down force, the self weight measure, and the gage wheel reaction force; and
- controlling the agricultural system based on the soil strength value.

12. The agricultural system of claim 11 and further comprising:
- receiving an indication of a detected furrow depth indicative of a depth of a furrow opened by a furrow opener on the row unit; and
- generating the soil strength metric with the soil strength value based on the detected furrow depth.

13. The agricultural system of claim 11, wherein the self weight detector comprises a weight sensor that senses the self weight of the row unit to generate the self weight measure.

14. The agricultural system of claim 11, wherein
- detecting the row unit down force comprises detecting the row unit down force applied to the row unit by the down force actuator during a current operation of the row unit on a field;
- detecting the force imparted by the ground on the gage wheel comprises detecting the force imparted by ground on the gage wheel during the current operation; and
- the self weight measure is defined prior to the current operation of the row unit on the field.

15. An agricultural system, comprising:
- a row unit comprising:

a row unit frame supporting a plurality of row unit components, the plurality of row unit components comprising:

a gage wheel, and one or more additional ground engaging components;

a down force actuator applying a row unit down force (RUDF) to the row unit on a field; and a down force detector detecting the RUDF;

a gage wheel reaction force detector configured to detect a gage wheel reaction force imparted by ground on the gage wheel;

an additional reaction force detector configured to detect an additional reaction force imparted by the ground on at least one component of the one or more additional ground engaging components;

at least one processor; and memory storing instructions executable by the at least one processor, wherein the instructions, when executed, cause the agricultural system to:

obtain a self weight of the row unit, the self weight representing at least a weight of the row unit frame;

calculating a soil strength value comprising the difference between (i) a calculated sum of at least the RUDF and the self weight and (ii) a calculated sum of at least the gage wheel reaction force and the additional reaction force; and generate a control signal that controls the agricultural system based on the soil strength value.

16. The agricultural system of claim 15, wherein the at least one component, of the one or more additional ground engaging components, comprises a furrow closer.

17. The agricultural system of claim 15, wherein the agricultural system is configured to:

generate a plurality of soil strength metrics for a plurality of geographic locations, wherein each respective soil strength metric, of the plurality of soil strength metrics, corresponds to a respective geographic location, of the plurality of geographic locations, and is generated based on a respective row unit down force at the respective geographic location and a respective gage wheel reaction force at the respective geographic location; and generate a soil strength map to represent the plurality of soil strength metrics at the plurality of geographic locations.

18. The agricultural system of claim 15, wherein the at least one component, of the one or more additional ground engaging components, comprises at least one of:

a row cleaner, or a seed firmer.

19. The agricultural system of claim 15, wherein the at least one component, of the one or more additional ground engaging components, comprises a colter wheel.

* * * * *